(12) United States Patent
Lin et al.

(10) Patent No.: US 11,690,935 B2
(45) Date of Patent: Jul. 4, 2023

(54) THERMOSENSITIVE PEPTIDE HYDROGEL

(71) Applicant: NATIONAL CHIAO TUNG UNIVERSITY, Hsinchu (TW)

(72) Inventors: Hsin-Chieh Lin, Taoyuan (TW); Imam Sahroni, Yogyakarta (ID)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 460 days.

(21) Appl. No.: 16/953,224

(22) Filed: Nov. 19, 2020

(65) Prior Publication Data
US 2021/0213172 A1    Jul. 15, 2021

(30) Foreign Application Priority Data
Jan. 10, 2020  (TW) .................. 109100929

(51) Int. Cl.
*A61L 27/52* (2006.01)
*A61L 27/18* (2006.01)
*A61L 27/22* (2006.01)
*A61L 27/50* (2006.01)
*C12N 5/00* (2006.01)

(52) U.S. Cl.
CPC ............... *A61L 27/52* (2013.01); *A61L 27/18* (2013.01); *A61L 27/22* (2013.01); *A61L 27/50* (2013.01); *C12N 5/0068* (2013.01); *A61L 2400/06* (2013.01); *C12N 2533/20* (2013.01); *C12N 2533/30* (2013.01)

(58) Field of Classification Search
CPC ....................................... A61L 27/52
See application file for complete search history.

(56) References Cited

U.S. PATENT DOCUMENTS 8,536,291 B2    9/2013  Fukushima et al.

FOREIGN PATENT DOCUMENTS

CN   108283729 B    6/2020
CN   108503860 B    8/2020

OTHER PUBLICATIONS

Melis Goktas et al., "Self-Assembled Peptide Amphiphile Nanofibers and PEG Composite Hydrogels as Tunable ECM Mimetic Microenvironment," Biomacromolecules, vol. 16, pp. 1247-1258, Mar. 9, 2015.
Rui Li et al., "Large and Small Assembly: Combining Functional Macromolecules with Small Peptides to Control the Morphology of Skeletal Muscle Progenitor Cells," Biomacromolecules, vol. 19, pp. 825-837, Feb. 1, 2018.
Ruirui Xing et al., "Self-Assembled Injectable Peptide Hydrogels Capable of Triggering Antitumor Immune Response," Biomacromolecules, vol. 18, pp. 3514-3523, Jul. 19, 2017.
(Continued)

*Primary Examiner* — Carlos A Azpuru
(74) *Attorney, Agent, or Firm* — Rabin & Berdo, P.C.

(57) ABSTRACT

The invention provides a thermosensitive peptide hydrogel, which comprises water, a polyether/polyol polymer and a peptide molecule. The peptide molecule has a structure represented by the following chemical formula (1).
Chemical Structure (1):

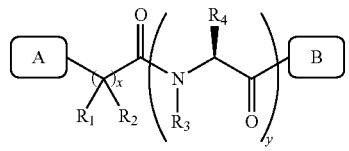

8 Claims, 22 Drawing Sheets

(56) References Cited

OTHER PUBLICATIONS

Teresa Fernández-Muiños et al., "Bimolecular based heparin and self-assembling hydrogel for tissue engineering applications," Acta Biomaterialia, vol. 16, pp. 35-48, Jan. 13, 2015.
Vivek A. Kumar et al., "Drug-Triggered and Cross-Linked Self-Assembling Nanofibrous Hydrogels," Journal of the American Chemical Society, vol. 137, pp. 4823-4830, Apr. 1, 2015.

Below CMC VS Above CMC

Solution — PEG 0.1 mM — PEG 0.8 mM — PEG 1.6 mM — PEG 3 mM — PEG 5 mM
Below CMC
CMC = 7.74 mM Above CMC — PEG 10 mM — PEG 16 mM — PEG 23 mM — PEG 30 mM
Become hydrogels Formation at 37 °C Viscous Solution Thermo DN Hydrogel

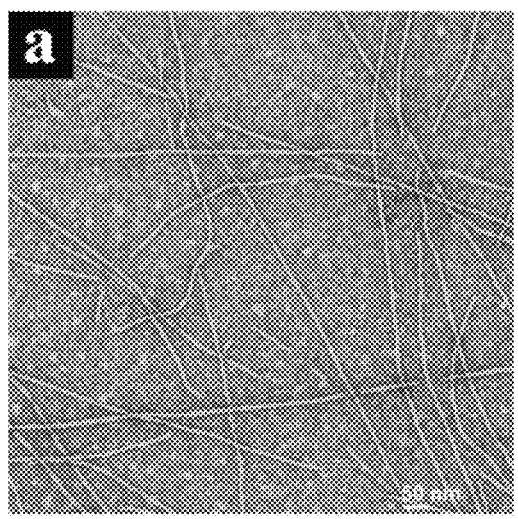 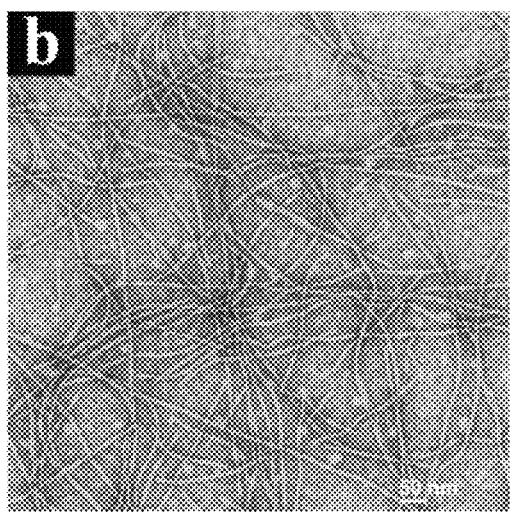
FIG. 19A  FIG. 19B
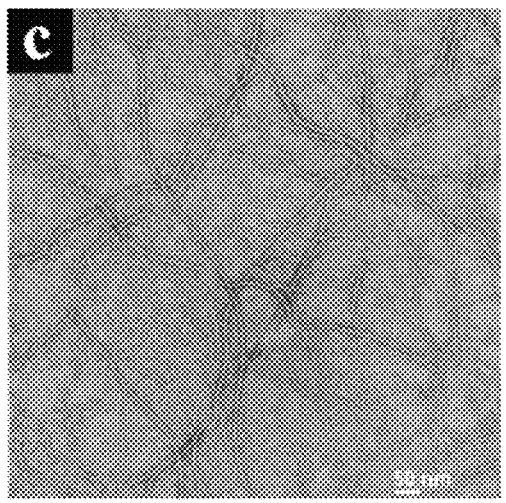 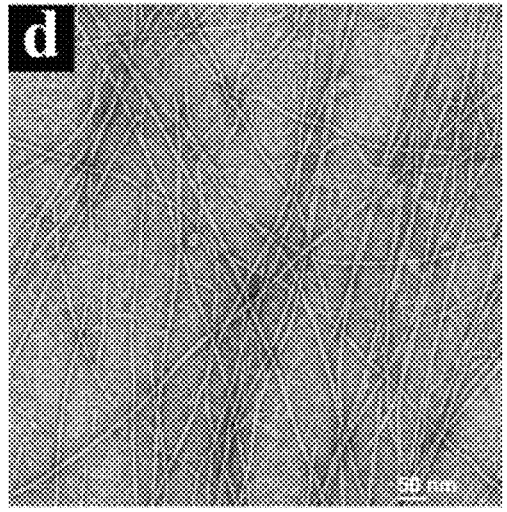
FIG. 19C  FIC. 19D
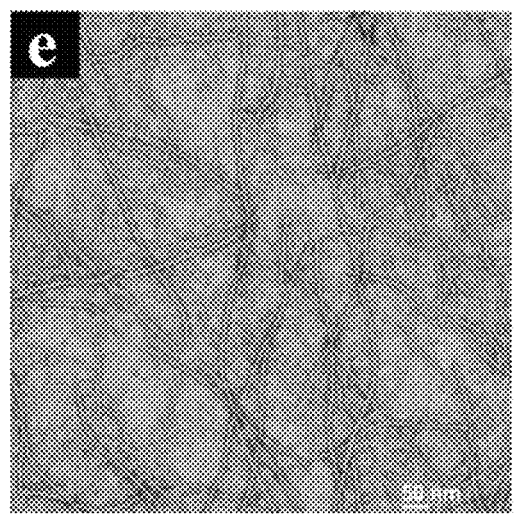 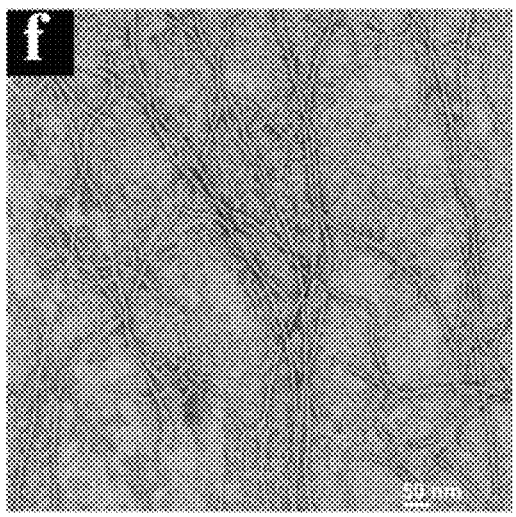
FIG. 19E  FIG. 19F

THERMOSENSITIVE PEPTIDE HYDROGEL

FIELD OF TECHNOLOGY

The invention relates to a thermosensitive peptide hydrogel, in particular to a thermosensitive peptide hydrogel having thermal reversibility.

BACKGROUND

Whether in tissue engineering, regenerative medicine, drug carriers, cancer models, or cell therapy, bio-compatible three-dimensional scaffolds are often used for experiments. At present, the main three-dimensional scaffolds are divided into thermosensitive hydrogel, Matrigel® and non-thermosensitive hydrogel, Collagen Type I Gels. However, these two types of hydrogels are of animal origin. Therefore, there are doubts as to whether or not they carry pathogens. At the same time, there are disadvantages such as being unable to accurately know the material composition and being expensive to sell. In addition, although Matrigel® is a thermosensitive hydrogel, it is liquid only at 4° C. So the cells can be mixed with it at low temperature, which makes the preparation inconvenient.

In recent years, there have been various improved methods for thermosensitive hydrogel. For example, collagen-containing materials are used to prepare hydrogels that can be gelled at 37° C., but they still have concerns about pathogens. Alternatively, chemical methods are used to synthesize thermosensitive polymers for conjugated proteins or peptides, but synthesizing these molecules requires multiple steps and therefore has a considerable cost. When polymers with thermosensitive properties, such as poly[N-isopropylacrylamide](PNIPAm) or other copolymers, are used, the polymers are often opaque, which causes some problems in the observation and analysis of biological experiments. In addition, most of the polymer materials can not have a nanofiber structure capable of simulating human extracellular matrix.

The commercially available PuraMatrix, which has a three-dimensional scaffold with a nanofiber structure, is composed of 16 amino acids, so the process is complicated, and the cost is quite high. In addition, because PuraMatrix is a non-thermosensitive hydrogel, it is inconvenient to mix with cells, and it is not easy to remove cells from the gel for analysis after the experiment is completed.

Therefore, how to provide a hydrogel that can avoid the problem of pathogen and has nanofiberous structure, thermosensitivity, thermal reversibility, injectability and properties that can be kept in water for a long time is still an urgent problem.

SUMMARY

In view of the above problems, an aspect of the invention is to provide a thermosensitive peptide hydrogel. By adjusting the structure of the peptide molecule, selecting different polymers, and adjusting the mixing ratio, etc., the peptide molecule and the ether or alcohol polymer (using polyethylene glycol with ether functional group and alcohol functional group as the testing polymer) are used to generate appropriate hydrogen bonds and weak interactions to produce new hydrogel materials and further improve the problems generated by the conventional techniques described above.

Accordingly, a thermosensitive peptide hydrogel is provided, which comprises water, a polymer of a polyether or a polyol, and a peptide molecule. The peptide molecule has a structure as shown in the following structural formula (1):

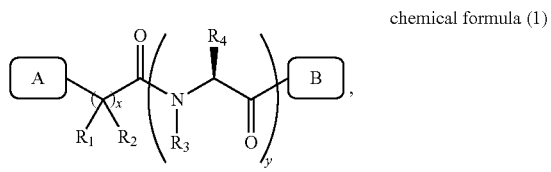

chemical formula (1)

wherein A is a molecular moiety with at least one aromatic group substituted with 0 to 5 halogen atoms, and the halogen atoms are independently fluorine, chlorine, bromine, or iodine atoms, and each halogen atom is identical or different; $R_1$ and $R_2$ are each independently hydrogen, a substituted or unsubstituted $C_1$-$C_{16}$ alkyl group; $R_3$ is hydrogen; $R_4$ is hydrogen, $C_1$-$C_{10}$ alkyl, $C_7$-$C_{10}$ aralkyl, $C_2$-$C_{10}$ alkylthioalkyl, $C_7$-$C_{10}$ hydroxyaralkyl, $C_6$-$C_{10}$ heteroaralkyl, $C_2$-$C_{10}$ carboxyalkane, $C_2$-$C_{10}$ guanidylalkyl or $C_1$-$C_{10}$ aminoalkyl; B is —OH, —OR$_5$, wherein $R_5$ is hydrogen, alkyl, aralkyl, alkylthioalkyl, hydroxyaralkyl, heteroaralkyl, carboxyalkyl, guanidylalkyl, glycosyl, or oligonucleic acid groups, and each $R_5$ is identical or different; x is an integer from 0 to 10, and each $R_1$ or $R_2$ is identical or different; and y is an integer from 1-20, and each $R_3$ or $R_4$ is identical or different.

According to some embodiments, a concentration of the above peptide molecules in the thermosensitive peptide hydrogel is at least 100 nM and not more than 30 wt %.

According to some embodiments, the halogen atoms are fluorine atom.

According to some embodiments, the polymer of the polyether or polyol may comprise, but is not limited to, poly(ethylene glycol), polyalkylene glycol, and polyvinyl alcohol (PVA), poly(propylene glycol), polyester polyol, polyphenylene oxide, poly(ethylene vinyl-co-alcohol) (EVOH), polysaccharide, or any combinations thereof.

According to some embodiments, the thermosensitive peptide hydrogel is a liquid at 2-30° C., and a hydrogel when above 30° C.

According to some embodiments, the thermosensitive peptide hydrogel has a storage modulus of 0.1-10$^7$ Pa at 37° C.

According to some embodiments, the thermosensitive peptide hydrogel is thermally reversible.

According to some embodiments, the glycosyl group contained in the peptide molecule is mannosyl, oligosaccharide, fructosyl, galactosyl, or any combinations thereof.

The thermosensitive peptide hydrogel has the following advantages:

(1) In this closure, by adjusting the functional group of the peptide molecule, different thermosensitive hydrogels can be prepared for different needs. In addition, using the peptide molecules above, only a suitable number of amino acids in the peptide is needed to prepare the hydrogels above. Therefore, the cost is relatively low, and the industrial production is easier.

(2) In this closure, the thermosensitive peptide hydrogel has adjustable mechanical properties by adding polyether polymers. Furthermore, because the storage modulus of the thermosensitive peptide hydrogel has a wide range, it can simulate the stiffness of various tissues in the human body.

(3) In this closure, the thermosensitive peptide hydrogel is in a liquid state at room temperature and is in a stable hydrogel state at 37° C. Therefore, only temperature needs to be adjusted without changing other parameters, such as the pH value, in the complicated procedure to change the state of the hydrogel. Hence, when performing cell culture and differentiation experiments, cells can be added at room temperature and the thermosensitive peptide hydrogel can be maintained in a hydrogel state in an incubator to facilitate various observations. Moreover, when the experiment is complete, the cells can be removed only through a simple cooling procedure.

(4) In this closure, the thermosensitive peptide hydrogel has a porous and nanofiber structure, so it can be applied to various fields such as tissue engineering, regenerative medicine, drug carriers, cancer models, and cell therapy.

(5) In this closure, the thermosensitive peptide hydrogel can restore the hydrogel to a liquid state within a few minutes, so it only needs to wait for a relatively short time. At the same time, compared with the commercially available hydrogel, the thermosensitive peptide hydrogel can be maintained in a phosphate buffered saline (PBS) for a relatively longer time.

(6) In this closure, the thermosensitive peptide hydrogel is not a traditional gelatin (i.e., animal glue, which does not contain ingredients of animal origin), so it can avoid the problem of pathogens of commercially available hydrogels. Besides, the composition of the thermosensitive peptide hydrogel can be clearly known to simplify the manufacturing process to maintain the identity of each batch during industrial production at the same time.

BRIEF DESCRIPTION OF THE DRAWINGS

In order to make it easier for those with ordinary skill in the art to understand the objectives, technical features, and benefits of some aspects of the invention more comprehensible, the attached drawings are described as follows:

FIGS. 19A-19F were TEM images of 1F-FF/PEG300, 1F-FF/PEG600, 1F-FF/PEG1000, 1F-FF/PEG1500, 1F-FF/PEG2000, and 1F-FF/PEG3000 according to some embodiments of the invention, respectively.

DESCRIPTION OF THE EMBODIMENTS

Figure 1:
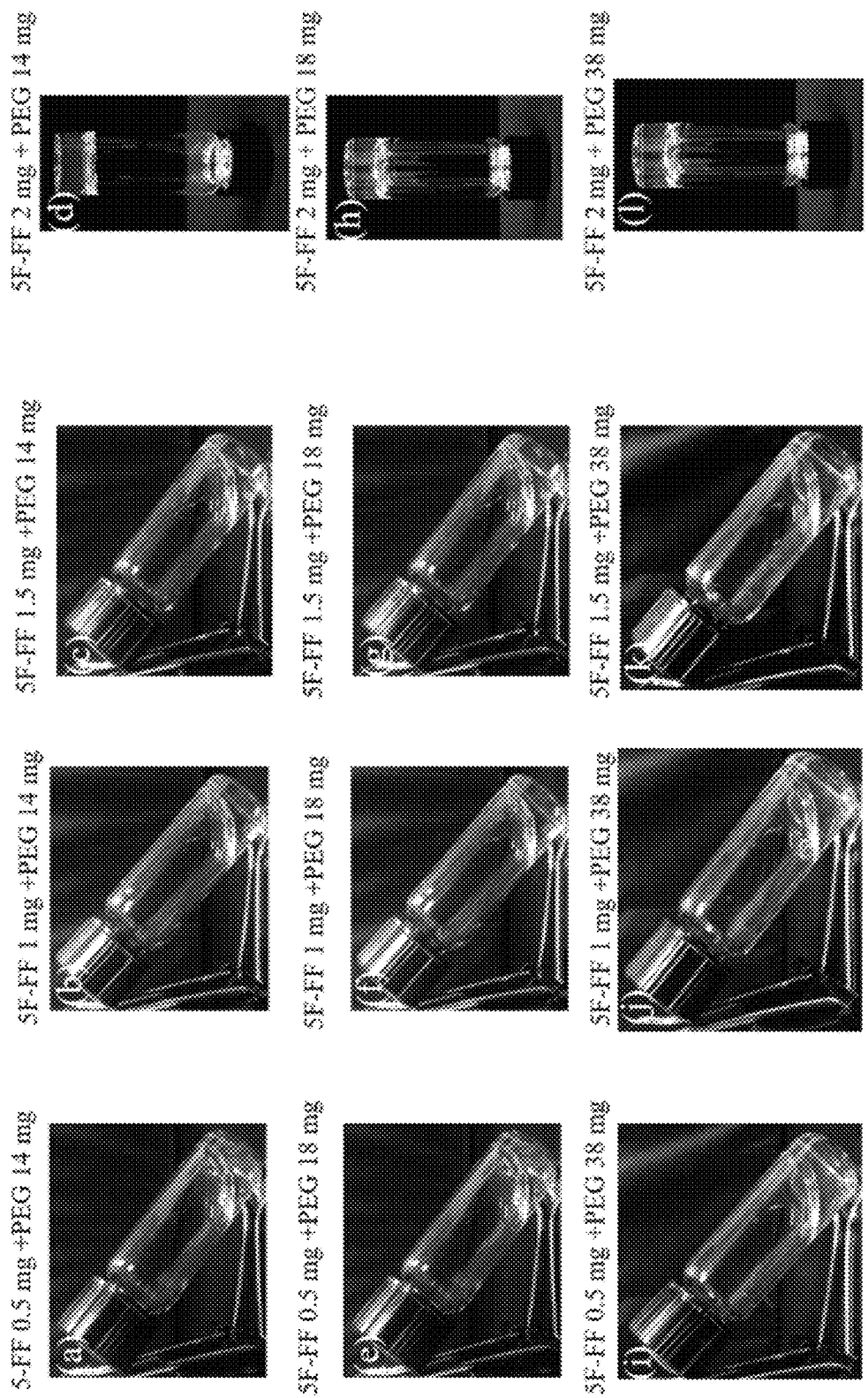
FIG. 1 showed optical images of hydrogels 5F-FF/PEG1500 with various mixing ratios of 5F-FF and PEG1500 at low concentrations according to some embodiments of the invention.
Figure 2A:
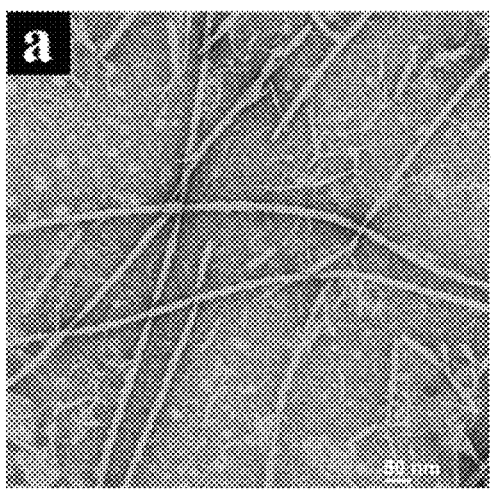
FIGS. 2A-2E were TEM images of hydrogels 5F-FF/PEG1500 at various ratios of 1 wt %, 2 wt %, 3 wt %, 4 wt %, and 5 wt % according to some embodiment of the invention.
Figure 2B:
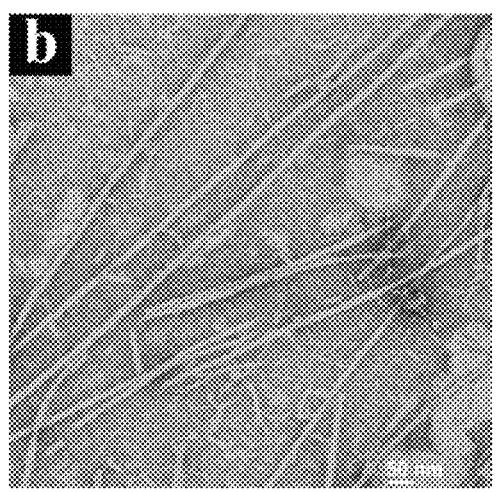
Figure 2C:
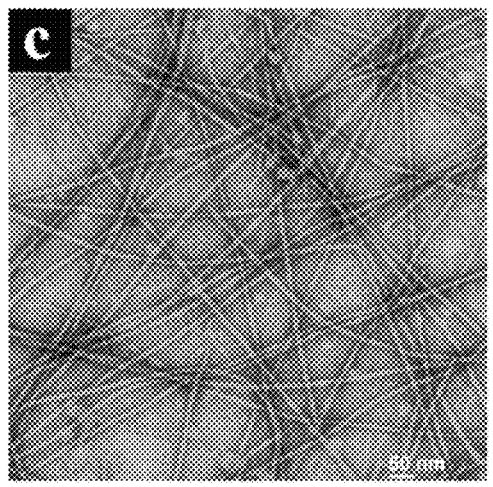
Figure 2D:
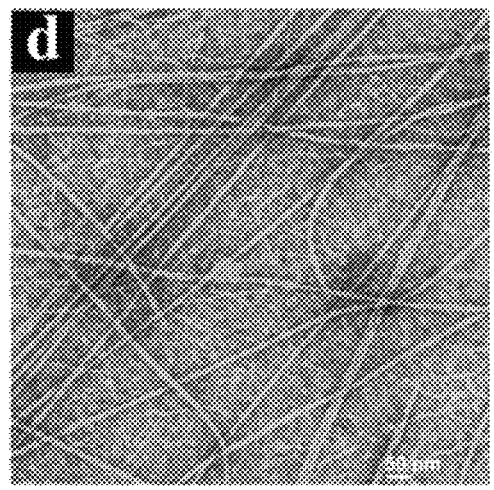
Figure 2E:
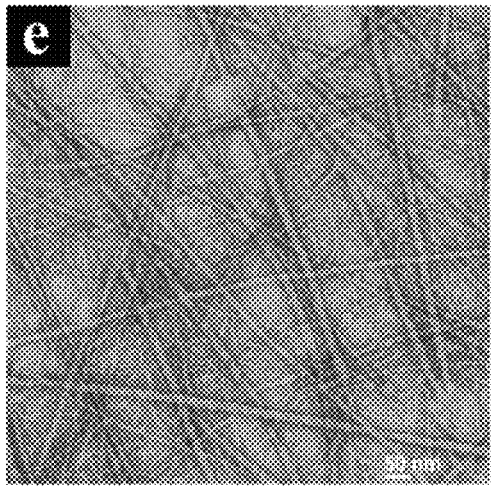

In order to make it easier for those with ordinary skill in the art to understand the objectives, technical features, and benefits after actual implementation, it will be described more detailed below with examples and drawings.

In some embodiments of the invention, a peptide molecule, represented by chemical formula (1), is prepared. Synthesis could be performed by solid phase peptide synthesis (SPPS) or any other method known to person skilled in the art.

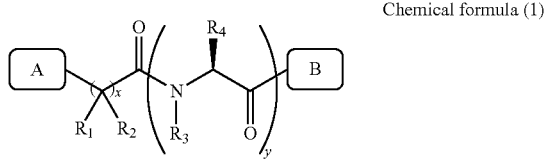

Chemical formula (1)

In some embodiments of the invention, A may be a molecular moiety with at least one aromatic group substituted with 0-5 halogen atoms. In some embodiments of the invention, the halogen atoms may be independently fluorine, chlorine, bromine or iodine atom, and each halogen atom may be identical or different. In some embodiments of the invention, due to considerations of cost and effectiveness, fluorine atom is chosen as the halogen atom.

In some embodiments of the invention, $R_1$ and $R_2$ may be each independently hydrogen or $C_1$-$C_{16}$ alkyl group. In some embodiments of the invention, $R_1$ and $R_2$ may be hydrogen atoms due to convenience of synthesizing.

In some embodiments of the invention, $R_3$ and $R_4$ may be each independently hydrogen atom, $C_1$-$C_{10}$ alkyl, $C_7$-$C_{10}$ aralkyl, $C_2$-$C_{10}$ alkylthioalkyl, $C_7$-$C_{10}$ hydroxyaralky, $C_6$-$C_{10}$ heteroaralkyl, $C_2$-$C_{10}$ carboxylalkyl, $C_2$-$C_{10}$ guanidinylalkyl or $C_1$-$C_{10}$ aminoalkyl. In some embodiments of the invention, $R_3$ is hydrogen atom due to convenience of synthesizing. In some embodiments of the invention, $R_4$ is benzyl due to advantages of controlling the hydrophilicity and hydrophobicity.

In some embodiments of the invention, B may be —OH, —$OR_5$ or —$N(R_5)_2$, and $R_5$ may be hydrogen, alkyl, aromatic hydrocarbon, alkylthioalkyl, hydroxyaromatic hydrocarbon, heteroaromatic hydrocarbon, carboxyalkyl, guanidino, aminoalkyl, glycosyl or oligonucleic acid groups, and each $R_5$ may be identical or different. In some embodiments of the invention, $R_5$ may be hydrogen, $C_1$-$C_{10}$ alkyl, $C_7$-$C_{10}$ aralkyl, $C_2$-$C_{10}$ alkylthioalkyl, $C_7$-$C_{10}$ hydroxyaralkyl, $C_6$-$C_{10}$ heteroaralkyl, $C_2$-$C_{10}$ carboxyalkyl or $C_2$-$C_{10}$ guanidino, glycosyl or oligonucleic acid groups. In some embodiments of the invention, the glycosyl may be mannosyl, oligosaccharide, fructosyl, or galactosyl. In some embodiments of the invention, the group of the oligosaccharide may be glucosamine.

In some embodiments of the invention, x may be an integer from 0 to 10, and each $R_1$ or each $R_2$ may be identical or different. In some embodiments of the invention, x may be 1 due to advantage of simplifying the synthesis. In some embodiments of the invention, y may be an integer from 1 to 20, and each $R_3$ or each $R_4$ may be identical or different. In some embodiments of the invention, y may be 2 due to advantage of lower cost.

In some embodiments of the invention, a polyether polymer is used to prepare a thermosensitive peptide hydrogel. The polyether polymers comprise poly(ethylene glycol) (referred to as PEG), polyphenylene oxide (referred to as PPO), or any combinations thereof.

In some embodiments of the invention, a peptide molecule and a polyethylene glycol are used to prepare for the polyethylene glycol, wherein the peptide molecule comprises a phenyl substituted by fluorine, and the polyethylene glycol comprises an ether group and an alcohol group. Analyses of the thermosensitive peptide hydrogel according to some embodiments of the invention is further adjusted by the number of fluorine atom substitutions, the molecular weight of PEG, the mixing ratio, the ambient temperature and other conditions.

Embodiment 1: Synthesis of Peptide Molecule 5F-FF

A peptide molecule 5F-FF (2,3,4,5,6-fluorobenzyl-diphenylalanine) was synthesized by solid phase peptide synthesis (SPPS) method, and 2-chlorotrityl chloride resin (100-200 mesh and 0.3-0.8 mmol/g) was used and treated twice by Fmoc-L-phenylalanine and pentafluoro benzeneacetic acid, wherein the synthesis method was shown in scheme (1).

Scheme (1)

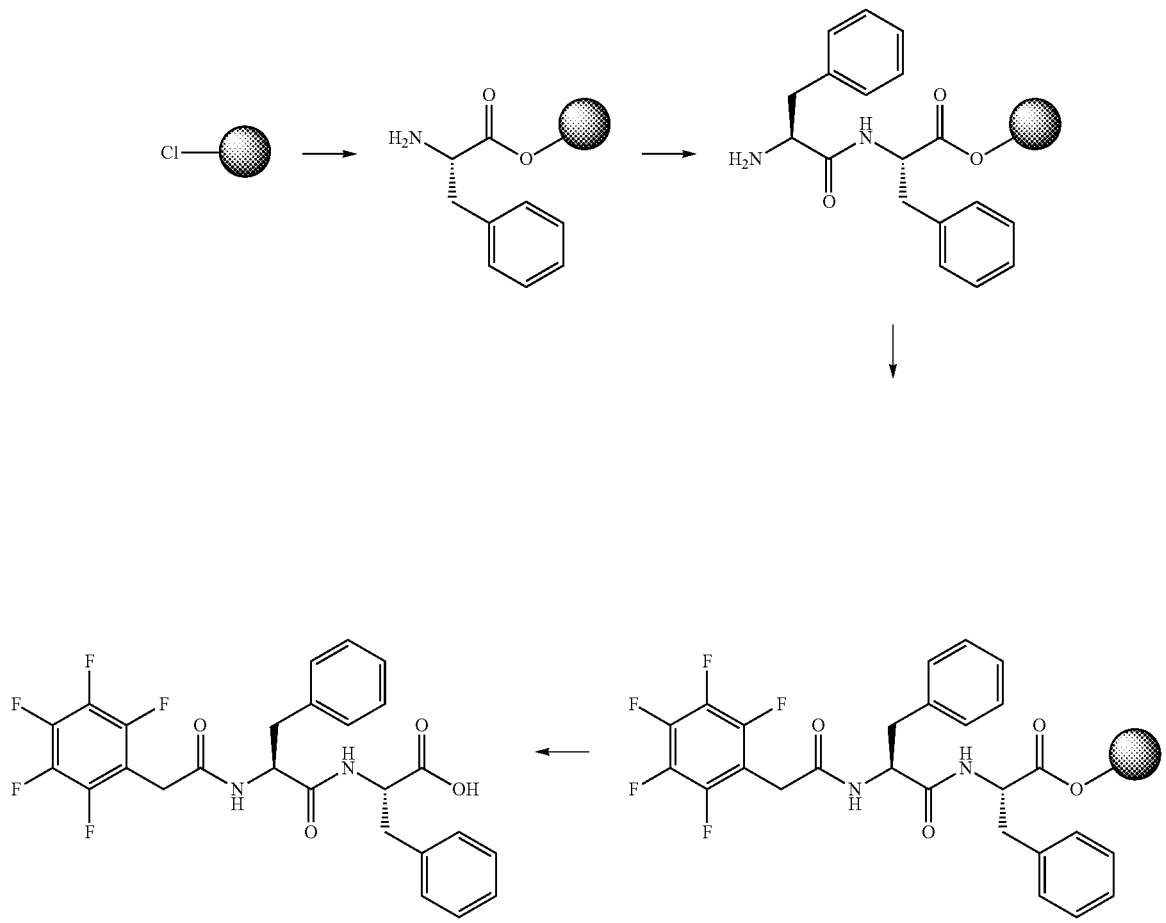

In detail, a resin (2.4 g) was swelled in anhydrous dichloromethane (DCM) for 30 minutes. Then, the Fmoc-L-phenylalanine (1.16 g, 3 mmol) was loaded on the resin in anhydrous N, N'-dimethylformamide (DMF) and N, N-diisopropylethylamine (DIEA) (1.3 mL, 7.5 mmol) for an hour. Then, a DMF solution containing 20% piperidine was added, wherein the reaction was performed for 30 minutes to remove a Fmoc protecting group and repeat the cleaning twice (2 minutes for each time).

Then, HBTU (0-[Benzotriazol-1-yl]-N, N, N', N'-tetramethyluronium hexafluorophosphate, 1.52 g, 4 mmol) and DIEA (1.7 mL, 10.0 mmol) were used as coupling agent. The Fmoc-L-phenylalanine (1.55 g, 4 mmol) was coupled with the free amine group for 30 minutes. Subsequently, the DMF solution containing 20% piperidine was added, wherein the reaction was performed for 30 minutes to remove the Fmoc protecting group and then repeat the cleaning twice (2 minutes for each time).

Finally, the HBTU (2.28 g, 6 mmol) and the DIEA (2.5 mL, 15.0 mmol) were used as coupling agents. The capping agent of pentafluorophenylacetic acid (1.356 g, 6 mmol) was coupled with the free amine group. Peptide derivatives were cleaved by 90% trifluoroacetic acid deionized aqueous solution for 3 hours. The product solution was air-dried, and diethyl ether was added to precipitate the target product. The solid was dried in vacuum to remove the remaining solvent (white solid: 0.56 g).

$^1$H NMR (300 MHz, DMSO-d6, 25° C.): δ=2.70-2.80 (m, $^1$H; $CH_2$ 2.90-3.15 (m, $^3$H; $CH_2$), 3.58 (s, 2H; CH2), 4.45-4.55 (m, $^1$H; CH), 4.55-4.65 (m, $^1$H; CH), 7.20-7.35 (m, $^{10}$H; CH), 8.35-8.50 (m, $^2$H; NH); MS [ESI]: m/z (%); Calculated value: 520.14; Measured value: 519.20 [MH]$^-$.

Embodiment 2: Synthesis of a Peptide Molecule 3F-FF

Accordingly, except for the replacement of the pentafluorophenylacetic acid by 2,4,6-fluorophenyl acetic acid (1.14 g, 6 mmol) to couple with the free amine groups, the rest conditions of the synthesis method of the peptide molecule 3F-FF were the same as the synthesis method of the peptide molecule 5F-FF, wherein the synthesis method of the peptide molecule 3F-FF was shown in scheme (2).

Scheme (2)

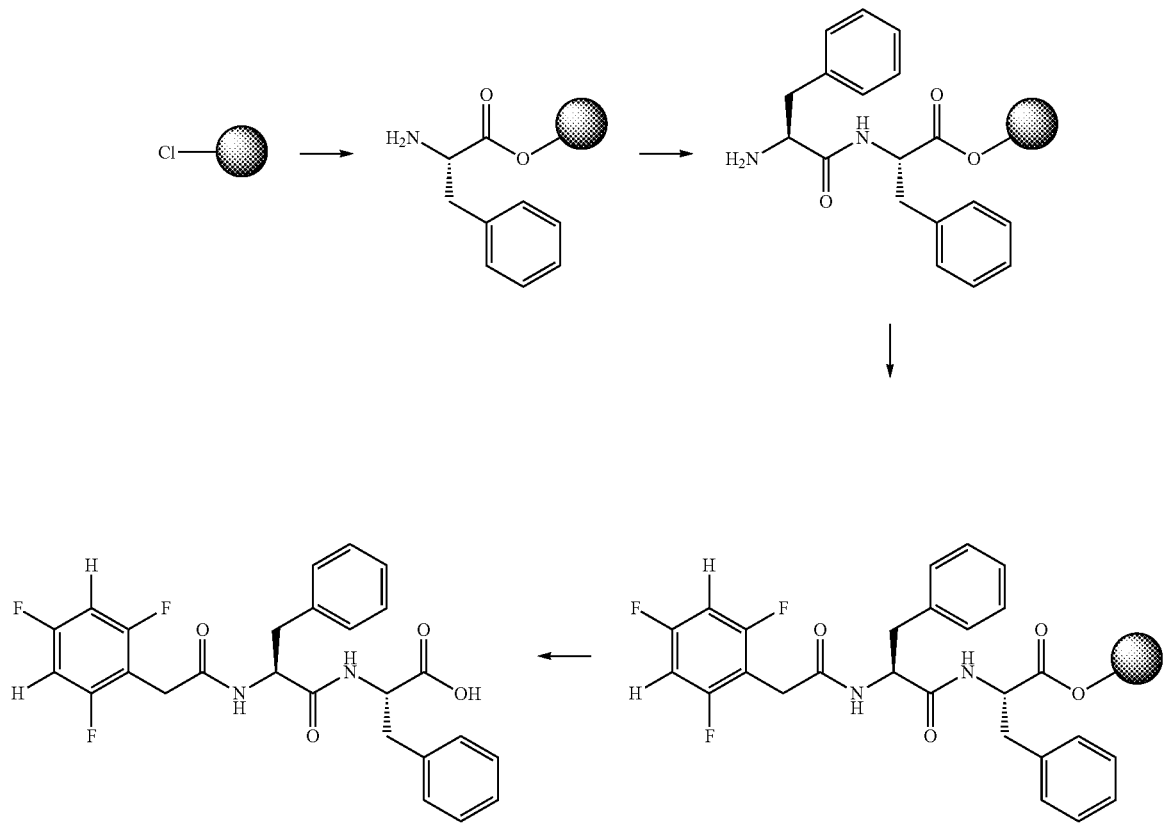

Moreover, the solid was dried in vacuum to remove the remaining solvent (white solid: 0.56 g). H NMR (300 MHz, DMSO-d6, 25° C.): δ=2.70-2.80 (m, $^1$H; $CH_2$), 2.90-3.15 (m, $^3$H; $CH_2$), 3.58 (s, 2H; $CH_2$), 4.45-4.55 (m, $^1$H; CH), 4.55-4.65 (m, $^1$H; CH), 7.20-7.35 (m, $^{10}$H; CH), 8.35-8.50 (m, $^2$H; NH); MS [ESI]: m/z (%); Calculated value: 484.18; Measured value: 482.10 [M−H]$^−$.

Embodiment 3: Synthesis of a Peptide Molecule 1F-FF

Accordingly, except for the replacement of the pentafluorophenylacetic acid by 4-fluorophenyl acetic acid (0.924 g, 6 mmol) to couple with the free amine groups, the rest conditions of the synthesis method of the peptide molecule 1F-FF were the same as the synthesis method of the peptide molecule 5F-FF, wherein the synthesis method of the peptide molecule 1F-FF was shown in scheme (3).

Scheme (3)

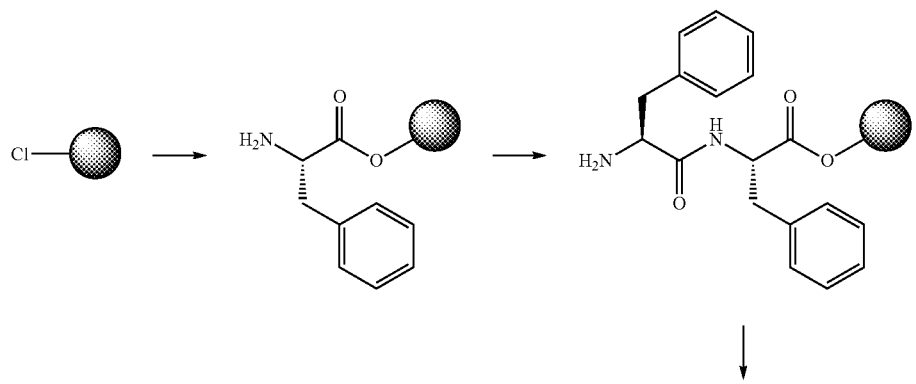

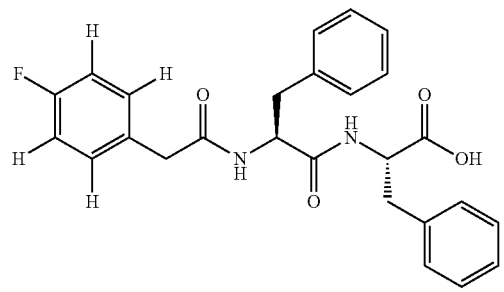
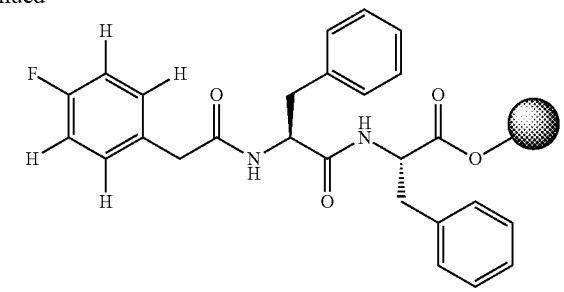

Moreover, the solid was dried in vacuum to remove the remaining solvent (white solid: 0.56 g). H NMR (300 MHz, DMSO-d6, 25° C.): δ=2.70-2.80 (m, $^1$H; CH$_2$), 2.90-3.15 (m, $^3$H; CH$_2$), 3.58 (s, 2H; CH$_2$), 4.45-4.55 (m, $^1$H; CH), 4.55-4.65 (m, $^1$H; CH), 7.20-7.35 (m, $^{10}$H; CH), 8.35-8.50 (m, $^2$H; NH); MS [ESI]: m/z (%); Calculated value: 448.18; Measured value: 447.10 [M−H]$^-$.

Embodiment 4: Synthesis of a Peptide Molecule 0F-FF

A peptide molecule 0F-FF (benzyl-diphenylalanine) was synthesized by the SPPS method, and 2-chlorotrityl chloride resin (100-200 mesh and 0.3-0.8 mmol/g) was used and treated twice by the Fmoc-L-phenylalanine and benzeneacetic acid, wherein the synthesis method of the peptide molecule 0F-FF was shown in scheme (4).

was performed for 20 minutes and then repeat the cleaning twice (2 minutes for each time).

Then, the HBTU (1.52 g, 4 mmol) and the DIEA (1.7 mL, 10.0 mmol) were used as the coupling agents. The Fmoc-L-phenylalanine (1.55 g, 4 mmol) was coupled with the free amine group for 30 minutes. Then, the DMF solution containing 20% piperidine was added, wherein the reaction was performed for 30 minutes to remove the Fmoc protecting group and then repeat the cleaning twice (2 minutes for each time).

Finally, the HBTU (2.28 g, 6 mmol) and the DIEA (2.5 mL, 15.0 mmol) were used as the coupling agents. The capping agent of the pentafluorophenylacetic acid (0.8163 g, 6 mmol) was coupled with the free amine group. The peptide derivatives were cleaved by the 90% trifluoroacetic acid deionized aqueous solution for 3 hours. The product solution was air-dried, and the diethyl ether was added to precipitate Scheme (4)

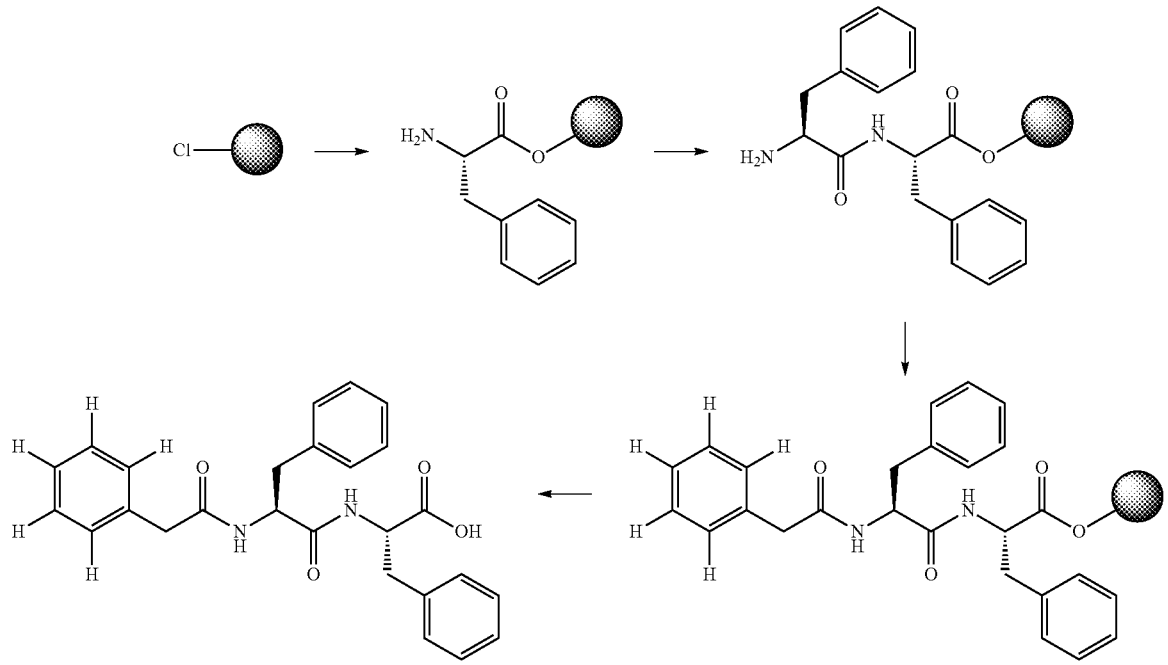

In detail, a resin (2.4 g) was swelled in the anhydrous DCM for 30 minutes. Then, Fmoc-L-phenylalanine (1.16 g, 3 mmol) was loaded on the resin in the anhydrous DMF and DIEA (1.3 mL, 7.5 mmol) for 1 hour. Then, a DMF solution containing 20% piperidine was added, wherein the reaction the target product. The solid was dried in vacuum to remove remaining solvent (white solid: 0.56 g).

$^1$H NMR (300 MHz, DMSO-d6, 25° C.): δ=2.70-2.80 (m, $^1$H; CH$_2$) 2.90-3.15 (m, $^3$H; CH$_2$), 3.58 (s, $^2$H; CH$_2$), 4.45-4.55 (m, $^1$H; CH), 4.55-4.65 (m, $^1$H; CH), 7.20-7.35

(m, $^{10}$H; CH), 8.35-8.50 (m, $^{2}$H; NH); MS [ESI]: m/z (%); Calculated value: 430.19; Measured value: 429.10 [M−H]$^{−}$.

Embodiment 5: Synthesis of a Peptide Molecule 5F-FFRGD

A peptide molecule PFB-FFRGD was synthesized by the SPPS method, as shown in chemical formula (4), wherein the 2-chlorotrityl chloride resin was used as a solid phase matrix.

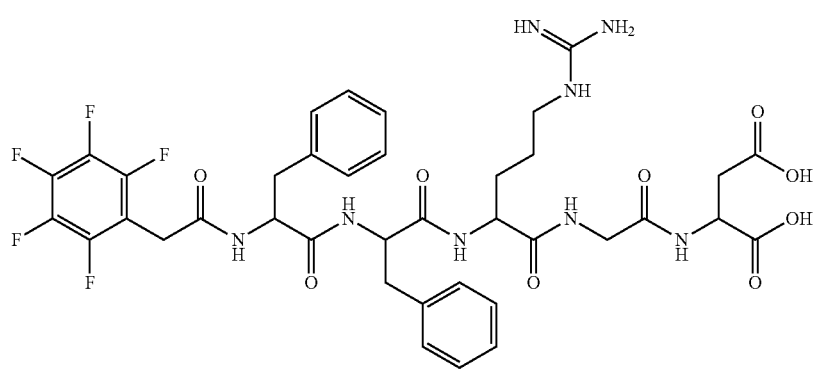

Chemical formula (4)

First, a resin (1.2 g, 2.0 mmol) was suspended and swelled in anhydrous DCM with continuously mixing for 30 minutes. Then, Fmoc-L-aspartic acid (2.0 mmol) and the DIEA (5.0 mmol) were dissolved in anhydrous DMF of appropriate amount, and then added to the resin for reacting about 60 minutes in order to attach amino acids to the resin. Subsequently, the DMF solution containing 20% piperidine was added, wherein the reaction was performed for 30 minutes to remove a Fmoc protecting group and then repeat the cleaning twice (2 minutes for each time).

Then, HBTU (2.0 mmol) and the DIEA (5.0 mmol) were used as coupling agents. A second amino acid Fmoc-L-glycine (2.0 mmol) was coupled with the free amine group, dissolved in the anhydrous DMF, and then added to the device of the SPPS method for reacting about 60 minutes. Subsequently, the DMF containing 20% piperidine was added, wherein the reaction was performed for 30 minutes to remove a Fmoc protecting group and repeat the cleaning twice.

Then, the HBTU (2.0 mmol) and the DIEA (5.0 mmol) were used as the coupling agents. A third amino acid Fmoc-L-arginine (2.0 mmol) was coupled with a free amine group and then dissolved in the anhydrous DMF. Then, it was added to the resin for reacting about 60 minutes. Subsequently, the DMF solution containing 20% piperidine was added, wherein the reaction was performed for another 30 minutes to remove the Fmoc protecting group and then repeat the cleaning twice.

Then, the HBTU (2.0 mmol) and the DIEA (5.0 mmol) were used as the coupling agents. A fourth amino acid Fmoc-L-phenylalanine (2.0 mmol) was coupled with a free amine group and then dissolved in the anhydrous DMF. Then, it was added to the resin for reacting about 60 minutes. Subsequently, the DMF solution containing 20% piperidine was added, wherein the reaction was performed for 30 minutes to remove a Fmoc protecting group and then repeat the cleaning twice.

Then, the HBTU (2.0 mmol) and the DIEA (5.0 mmol) were used as the coupling agents. A fifth amino acid Fmoc-L-phenylalanine (2.0 mmol) was coupled with a free amine group and then dissolved in the anhydrous DMF. Then, it was added to the resin for reacting about 60 minutes. Subsequently, the DMF solution containing 20% piperidine was added, wherein the reaction was performed for 30 minutes to remove a Fmoc protecting group and then repeat the cleaning twice.

Then, the capping agent pentafluorophenylacetic acid (3.0 mmol), the coupling agent HBTU (3.0 mmol) and the DIEA (7.5 mmol) were dissolved in the anhydrous DMF of appropriate amount, and then the solution was added to the amine combined with the resin, wherein the reaction was performed overnight. Finally, the solvent was removed. The obtained resin was cleaved by deionized water of 90% trifluoroacetic acid and a solution of triisopropylsilane (TIPS) for 3 hours. The product solution was air-dried, and diethyl ether was added to precipitate the target product.

$^{1}$H NMR (300 MHz, [d$_{6}$] DMSO): δ=7.32-7.12 (m, 10H, Ar—H), 4.60-4.45 (m, $^{3}$H), 4.32-4.15 (m, $^{1}$H), 3.8-3.69 (m, $^{2}$H), 3.53 (s, $^{2}$H), 3.16-2.90 (m, $^{4}$H), 2.87-2.61 (m, $^{4}$H), 1.78-1.69 (m, $^{1}$H), 1.60-1.39 (m, $^{3}$H); 13C NMR (75 MHz, [d$_{6}$] DMSO): δ=173.3, 172.8, 172.0, 172.3, 171.9, 171.8, 169.4, 167.3, 157.7, 147.3, 144.1, 141.9, 139.2, 138.6, 136.2, 130.2, 130.1, 129.0, 128.8, 127.2, 127.2, 127.1, 111.1, 54.9, 53.2, 49.6, 42.5, 38.5, 38.2, 37.2, 30.2, 29.5, 28.8. HRMS: Calculated value: m/z: 848.2917, Measured value: 849.3005 [M+H]$^{+}$.

Embodiment 6: Synthesis of a Peptide Molecule 5F-FFRGE

A peptide molecule PFB-FFRGE was synthesized by the SPPS method, as shown in chemical formula (5). The synthesis method of the peptide molecule PFB-FFRGE was basically the same as the corresponding part of the peptide molecule PFB-FFRGD in the Embodiment 5, except for the amino acid first added was different. During the synthesis of the peptide molecule PFB-FFRGE, the first amino acid Fmoc-L-aspartic acid (2.0 mmol) used in the peptide molecule PFB-FFRGD of the Embodiment 5 was replaced with Fmoc-L-glutamic acid (2.0 mmol).

Chemical formula (5)

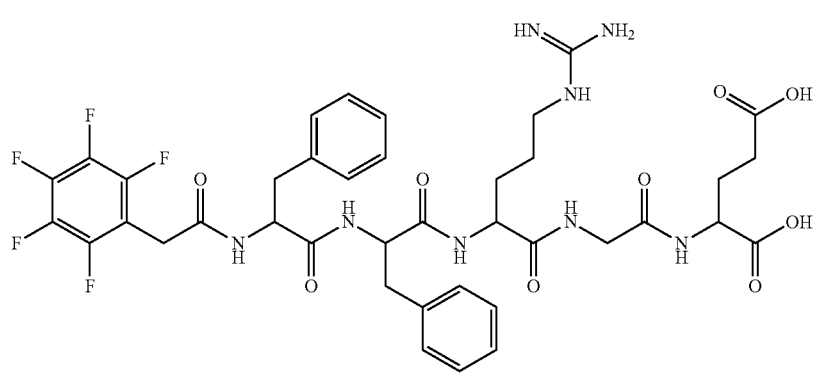

$^1$H NMR (300 MHz, [d$_6$] DMSO): δ=7.32-7.15 (m, $^{10}$H, Ar—H), 4.60-4.45 (m, $^2$H), 4.32-4.15 (m, $^2$H), 3.82-3.69 (m, $^3$H), 3.54 (s, $^2$H), 3.16-2.90 (m, $^3$H), 2.87-2.61 (m, $^2$H), 2.25 (t, J=7.5 Hz, $^2$H), 2.05-1.90 (m, $^1$H), 1.82-1.65 (m, $^2$H), 1.60-1.39 (m, $^3$H); 13C NMR (75 MHz, [d$_6$] DMSO): δ=174.7, 174.1, 172.3, 172.0, 171.9, 169.6, 167.3, 157.7, 147.3, 144.1, 139.0, 138.6, 136.0, 130.2, 130.1, 129.0, 128.8, 127.2, 127.2, 127.1, 111.1, 54.9, 53.3, 52.2, 42.6, 38.5, 38.2, 31.0, 30.1, 29.4, 27.4, 25.7. HRMS: Calculated value: m/z: 862.3073, Measured value: 863.3145 [M+H]$^+$.

Embodiment 7: Synthesis of a Peptide Molecule 5F-FFGHAVD

A peptide molecule PFB-FFGHAVD was synthesized by the SPPS method, as shown in chemical formula (6), wherein the 2-chlorotrityl chloride resin was used as solid phase matrix.

First, a resin (1.2 g, 2.0 mmol) was suspended and swelled in the anhydrous DCM with continuously mixing for 30 minutes. Then, Fmoc-L-aspartic acid (2.0 mmol) and DIEA (5.0 mmol) were dissolved in anhydrous DMF of appropriate amount, and then added to the resin for reacting about 60 minutes in order to attach amino acids to the resin. Subsequently, the DMF solution containing 20% piperidine was added, wherein the reaction was performed for 30 minutes to remove a Fmoc protecting group and then repeat the cleaning twice (2 minutes for each time).

Then, HBTU (2.0 mmol) and the DIEA (5.0 mmol) were used as coupling agents. A second amino acid Fmoc-L-valine (2.0 mmol) was coupled with a free amine group, dissolved in the anhydrous DMF, and then added to the device of the SPPS method for reacting about 60 minutes. Subsequently, the DMF solution containing 20% piperidine was added, wherein the reaction was performed for 30 minutes to remove a Fmoc protecting group and repeat the cleaning twice.

Then, the HBTU (2.0 mmol) and the DIEA (5.0 mmol) were used as coupling agents. A third amino acid Fmoc-L-alanine (2.0 mmol) was coupled with a free amine group, dissolved in the anhydrous DMF, and then added to the resin for reacting about 60 minutes. Subsequently, the DMF solution containing 20% piperidine was added, wherein the reaction was performed for 30 minutes to remove a Fmoc protecting group and repeat the cleaning twice.

Then, the HBTU (2.0 mmol) and the DIEA (5.0 mmol) were used as coupling agents. A fourth amino acid Fmoc-L-histidine (2.0 mmol) was coupled with a free amine group, dissolved in the anhydrous DMF, and then added to the resin for reacting about 60 minutes. Subsequently, the DMF solution containing 20% piperidine was added, wherein the Chemical formula (6)

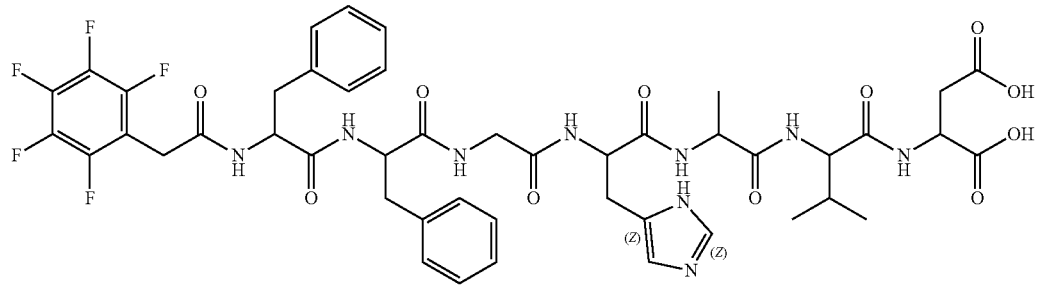

reaction was performed for 30 minutes to remove a Fmoc protecting group and repeat the cleaning twice.

Then, the HBTU (2.0 mmol) and the DIEA (5.0 mmol) were used as coupling agents. A fifth amino acid Fmoc-L-glycine (2.0 mmol) was coupled with a free amine group, dissolved in the anhydrous DMF, and then added to the resin for reacting about 60 minutes. Subsequently, the DMF solution containing 20% piperidine was added, wherein the reaction was performed for 30 minutes to remove a Fmoc protecting group and repeat the cleaning twice.

Then, the HBTU (2.0 mmol) and the DIEA (5.0 mmol) were used as coupling agents. A sixth amino acid Fmoc-L-phenylalanine (2.0 mmol) was coupled with a free amine group, dissolved in the anhydrous DMF, and then added to the resin for reacting about 60 minutes. Subsequently, the DMF solution containing 20% piperidine was added, wherein the reaction was performed for 30 minutes to remove a Fmoc protecting group and repeat the cleaning twice.

Then, the HBTU (2.0 mmol) and the DIEA (5.0 mmol) were used as coupling agents. A seventh amino acid Fmoc-L-phenylalanine (2.0 mmol) was coupled with a free amine group, dissolved in an anhydrous DMF, and then added to the resin for reacting about 60 minutes. Subsequently, the DMF solution containing 20% piperidine was added, wherein the reaction was performed for 30 minutes to remove a Fmoc protecting group and repeat the cleaning twice.

Then, the capping agent pentafluorophenylacetic acid (3.0 mmol), the coupling agent HBTU (3.0 mmol) and the DIEA (7.5 mmol) were dissolved in the anhydrous DMF of appropriate amount, and then the solution was added to the amine combined with the resin, wherein the reaction was performed overnight. Finally, the solvent was removed. The obtained resin was cleaved by deionized water of 90% trifluoroacetic acid and a solution of triisopropylsilane (TIPS) for 3 hours. The product solution was air-dried, and diethyl ether was added to precipitate the target product.

$^1$H NMR (300 MHz, [d$_6$] DMSO): δ=8.95 (s, $^1$H), 7.32 (s, $^1$H), 7.32-7.12 (m, $^{10}$H, Ar—H), 4.70-4.61 (m, $^1$H) 4.60-4.45 (m, $^3$H), 4.42-4.31 (m, $^1$H), 4.18-4.28 (m, $^1$H), 3.72 (d, J=5.4 Hz, $^2$H), 3.54 (s, $^2$H), 3.1-2.90 (m, $^4$H), 2.87-2.61 (m, $^4$H), 1.95-2.05 (m, $^1$H), 1.24 (d, J=6.9 Hz, $^3$H), 1.08 (t, J=7.2 Hz, $^1$H), 0.89-0.67 (m, $^6$H); $^1$C NMR (75 MHz, [d$_6$] DMSO): δ=173.1, 172.7, 172.1, 171.8, 171.4, 171.0, 169.9, 169.1, 166.9, 159.2, 158.8, 146.9, 138.7, 138.1, 138.0, 135.4, 134.1, 129.6, 128.5, 128.3, 126.7, 117.6, 110.6, 110.3, 57.8, 54.5, 54.4, 51.8, 49.0, 42.5, 37.9, 36.3, 31.2, 29.0, 27.8, 19.5, 18.2. EMS: Calculated value: m/z: 999.3, Measured value: 1000.4 [M+H].

Embodiment 8: Synthesis of a Peptide Molecule 5F-FFGHAVDI

A peptide molecule PFB-FFGHAVDI was synthesized by the SPPS method, as shown in chemical formula (7), wherein the 2-chlorotrityl chloride resin was used as solid phase matrix.

First, a resin (1.2 g, 2.0 mmol) was suspended and swelled in the anhydrous DCM with continuously mixing for 30 minutes. Then, Fmoc-L-heterophosphate (2.0 mmol) and DIEA (5.0 mmol) were dissolved in anhydrous DMF of appropriate amount, and then added to the resin for reacting about 60 minutes in order to attach amino acids to the resin. Subsequently, the DMF solution containing 20% piperidine was added, wherein the reaction was performed for 30 minutes to remove a Fmoc protecting group and then repeat the cleaning twice (2 minutes for each time).

Then, the adding sequence of the amino acids from the second to the eighth was the same as the adding sequence of the amino acids from the first to the seventh of the peptide molecule PFB-FFGHAVD in Embodiment 7. Therefore, regarding the subsequent synthesis steps of the peptide molecule PFB-FFGHAVDI, please refer to the related content of the peptide molecule PFB-FFGHAVD in Embodiment 7 which will not be repeated here.

$^1$H NMR (300 MHz, [d$_6$] DMSO): δ=8.96 (s, $^1$H), 7.38 (s, $^1$H), 7.32-7.15 (m, $^{10}$H, Ar—H), 4.71-4.48 (m, $^4$H) 4.43-4.28 (m, $^1$H), 4.15-4.27 (m, $^3$H), 3.72 (d, J=5.4 Hz, 2H), 3.54 (s, $^2$H), 3.1-2.90 (m, $^5$H), 2.87-2.61 (m, $^3$H), 1.89-2.05 (m, $^1$H), 1.83-1.69 (m, $^1$H), 1.42-1.31 (m, $^1$H), 1.29-1.08 (m, $^6$H), 0.89-0.75 (m, $^1$H); $^1$C NMR (75 MHz, [d$_6$] DMSO): δ=173.1, 172.9, 172.8, 171.2, 171.9, 169.9, 169.1, 169.0, 168.4, 166.9, 159.2, 158.8, 138.1, 135.1, 134.2, 130.0, 129.6, 129.5, 128.9, 128.6, 128.5, 128.3, 127.6, 126.6, 119.6, 117.6, 115.6, 57.9, 56.7, 54.5, 54.4, 53.6, 51.7, 49.8, 49.0, 37.9, 37.3, 36.9, 36.3, 31.2, 25.0, 19.6, 18.1, 15.8, 11.7. EMS: Calculated value: m/z: 1112.4, Measured value: 1113.4 [M+H]$^+$.

Preparation of Hydrogel and Sol-Gel Transition

In a glass bottle of 2 mL (diameter 10 mm) with a screw cap, different compounds with different concentrations were weighed to perform the gelation. A sodium hydroxide solution was added to the suspension in order to adjust the pH value, and vortex and treatment of the sonication were alternately used until a clear compound solution was obtained. Polyethylene glycols having different molecular weights such as 300 g/mol, 600 g/mol, 1000 g/mol, 1500 g/mol, 2000 g/mol, and 3000 g/mol, etc. were also dissolved in the deionized water in order to obtain the polyethylene glycol solution, and the desired concentrations were further controlled. After the polyethylene glycols were completely dissolved, the polyethylene glycol solution was then mixed with the compound solution in order to obtain a compound/PEG solution. By adding hydrochloric acid dropwise, the pH value of the compound/PEG solution was adjusted to a neutral pH value of 7.0-7.4.

Chemical formula (7)

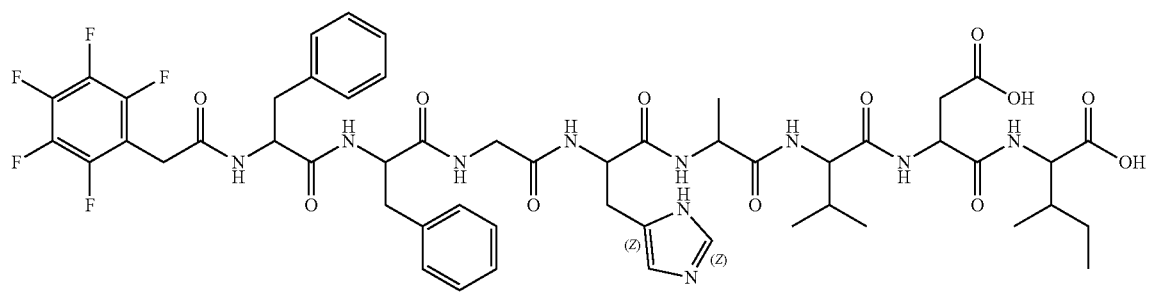

Gel formation was determined by a vial inverting method. After the equilibrium at room temperature, a glass bottle with the sample was immersed into a water bath of 37° C. in equilibrium or in an incubator of 37° C. for 30 minutes. After flipping the glass bottle, the sol-gel transition was determined. If the sample without floating was observed within 1 minute, the sample was considered as a gel. As for the temperature-dependent measurements, the temperature was gradually increased with an increment of 1° C., which represented that the accuracy of the sol-gel transition temperature was within ±1° C. Each of the temperature data point represented an average temperature of three measurements. At a physiologically relevant temperature of 37° C., the gelation time as a function of the concentration of the block copolymer was measured in the water bath of 37° C.

Hydrogel Degradation

Hydrogel degradation was performed in a phosphate buffered solution (PBS) at 37° C. with 5% of $CO_2$. In a 4 mL glass bottle, various 0.3 mL hydrogels were prepared, and 3 mL PBS was added to each of the glass bottles having the hydrogel. At some specific data points, the PBS was removed. The hydrogel was freeze-dried by the freeze-drying method, and the hydrogel degradation rate was calculated according to the following Formula (1), $$W(\%) = \frac{Wd - Wi}{Wi} \times 100\%, \quad \text{Formula (1)}$$

wherein W (%) represented the hydrogel degradation rate, Wi represented the initial weight of the hydrogel at day 0, and $W_d$ represented the dry weight of the hydrogel at day of a specific number.

Cell Viability Test

The biocompatibilities of different peptide molecules were measured by a cell viability test (MTT assay). hMSC (3A6) cells were seeded in a 24-well plate with a density of 50,000 cells in each well, and the hMSC (3A6) cells were cultured for 24 hours, wherein the 24-well plate comprises a culture medium (DMEM) of 0.5 mL, and the DMEM comprises 10% FBS and 1% penicillin. When seeded in the cells, each of the wells was added with the compounds of different concentrations (0.5 and 5 wt %). After 24 and 48 hours, the original culture medium was replaced by a fresh culture medium, wherein the fresh culture medium was supplemented with a MTT reagent of 0.5 mL (4 mg/mL). After another 4 hours, the culture medium containing the MTT reagent was removed, and DMSO (0.5 mL per well) was then added in order to dissolve formazan crystals. Each of the 24-well plate was transferred to a 96-well plate. The optical density of the cells was measured at 595 nm by a light absorption plate reader (Sunrise, DV990/BV4 GDV Programmable MPT reader). The cells without treated by the compounds were used as the control group. The cell viability percentage, that is, viability (%), of the cells was calculated according to the following Formula (2).

$$\text{Viability (\%)} = \frac{OD_{sample}}{OD_{control}} \times 100\%, \quad \text{Formula (2)}$$

wherein $OD_{sample}$ represented the optical density of the sample, and $OD_{control}$ represented the optical density of the control group.

In some embodiments of the invention, a compound 5F-FF was selected, and a PEG with a molecular weight of 1500 was selected for further testing, wherein the mixing ratio and the state of the 5F-FF/PEG1500 at 37° C. were shown in Table 1. The state was a sol solution state or a gel state.

TABLE 1

| Samples | Mixing ratio (wt %/wt %) | Mixing ratio (mg) | Total volume (mL) | pH | State at 37° C. |
|---|---|---|---|---|---|
| 1 wt % 5F-FF/PEG1500 | (0.5:0.5) | (2:2) | 0.4 | 7.0 | Sol |
| 2 wt % 5F-FF/PEG1500 | (0.5:1.5) | (2:6) | 0.4 | 7.0 | Gel |
| 3 wt % 5F-FF/PEG1500 | (0.5:2.5) | (2:10) | 0.4 | 7.0 | Gel |
| 4 wt % 5F-FF/PEG1500 | (0.5:3.5) | (2:14) | 0.4 | 7.0 | Gel |
| 5 wt % 5F-FF/PEG1500 | (0.5:4.5) | (2:18) | 0.4 | 7.0 | Gel |

As shown in Table 1, the samples regardless of the mixing ratio were all in a solution state after stirred overnight at 25° C. However, when the temperature was raised to 37° C., except for 1 wt % 5F-FF/PEG1500, the samples of the remaining mixing ratios were all converted into hydrogels after 30 minutes. It was worth noting that at the temperature of 25-37° C., the 5F-FF/PEG1500 with a low concentration of 2-5 wt % will undergo thermosensitive gelation. Specifically, all hydrogels were transparent.

In some embodiments of the invention, accordingly, in order to further analyze the characteristics of a supramolecular hydrogel triggered by the 5F-FF/PEG1500 at a low concentration, the 5F-FF with a concentration from less than to greater than a critical gelation concentration (CGC) and the PEG1500 with a concentration from less than to greater than the critical micelle concentration (CMC) were used for analysis. The mixing ratios were shown in Table 2, and the results were shown in FIG. 1. FIG. 1 showed optical images of hydrogels 5F-FF/PEG1500 with various mixing ratios of F5F-FF and PEG1500 at low concentration according to some embodiments of the invention.

TABLE 2

| Samples | 5F-FF/PEG1500 Mixing ratio (mg/mg) | Total volume (mL) | pH | State at 37° C. |
|---|---|---|---|---|
| (a) | (0.5:14) | 0.4 | 7.0 | Sol |
| (b) | (1:14) | 0.4 | 7.0 | Sol |
| (c) | (1.5:14) | 0.4 | 7.0 | Sol |
| (d) | (2:14) | 0.4 | 7.0 | Gel |
| (e) | (0.5:18) | 0.4 | 7.0 | Sol |
| (f) | (1:18) | 0.4 | 7.0 | Sol |
| (g) | (1.5:18) | 0.4 | 7.0 | Sol |
| (h) | (2:18) | 0.4 | 7.0 | Gel |
| (i) | (0.5:38) | 0.4 | 7.0 | Sol |
| (j) | (1:38) | 0.4 | 7.0 | Sol |
| (k) | (1.5:38) | 0.4 | 7.0 | Sol |
| (l) | (2:38) | 0.4 | 7.0 | Gel |

Referring to FIG. 1 and Table 2, it showed that under the conditions of the 5F-FF of 0.5-2 mg (0.125-0.5 wt %) and the PEG1500 of 14-38 mg (3.5-9.5 wt %), that is, the result for the hydrogel preparation at a concentration of below-CGC/above-CGC showed that when an initial concentration of the 5F-FF was less than the CGC (0.5 wt %), no matter at 25 or 37° C., no gel could be formed. However, each of the 5F-FF with an initial concentration of greater than the CGC was a solution at 25° C., but was a hydrogel at 37° C. Therefore, the CGC was very important for 5F-FF/PEG1500 supramolecular thermosensitive hydrogel.

In some embodiments of the invention, accordingly, in order to understand the morphology of a thermosensitive double-network (DN) fiber hydrogel based on 5F-FF/

PEG1500, the TEM was applied in order to analyze the results for the samples of 1, 2, 3, 4, and 5 wt % as shown in Table 1. The results were shown in FIG. 1. FIGS. 2A-2E were TEM images of hydrogels 5F-FF/PEG1500 at various ratios of 1 wt %, 2 wt %, 3 wt %, 4 wt %, and 5 wt % according to some embodiment of the invention.

Referring to FIGS. 2A-2E, it showed that the 5 wt % 5F-FF/PEG1500 hydrogel had a uniformly arranged fiber structure.

Figure 3:
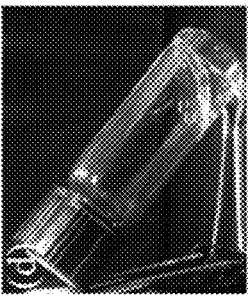
FIG. 3 showed optical images of hydrogels 5F-FF/PEG1500 with different mixing ratios according to some embodiments of the invention.

In some embodiments of the invention, accordingly, the 5 wt % 5F-FF/PEG1500 hydrogel was analyzed by a hierarchical mechanism analysis based on a double-network hydrogel (DNH) of the 5F-FF/PEG1500, wherein the mixing ratios were shown in Table 3, and the results were shown in FIG. 3. FIG. 3 showed optical images of hydrogels 5F-FF/PEG1500 with different mixing ratios according to some embodiments of the invention.

TABLE 3

| Samples | 5F-FF/PEG1500 Mixing ratio (wt %/wt %) | PEG Concentration (mM) | Total volume (mL) | pH | State at 37° C. |
|---|---|---|---|---|---|
| (a) | (0.5:0.003) | 0.1 | 0.4 | 7.0 | Sol |
| (b) | (0.5:0.125) | 0.8 | 0.4 | 7.0 | Sol |
| (c) | (0.5:0.25) | 1.6 | 0.4 | 7.0 | Sol |
| (d) | (0.5:0.5) | 3 | 0.4 | 7.0 | Sol |
| (e) | (0.5:1) | 5 | 0.4 | 7.0 | Sol |
| (f) | (0.5:1.5) | 10 | 0.4 | 7.0 | Gel |
| (g) | (0.5:2.5) | 16 | 0.4 | 7.0 | Gel |
| (h) | (0.5:3.5) | 23 | 0.4 | 7.0 | Gel |
| (i) | (0.5:4.5) | 30 | 0.4 | 7.0 | Gel |

Referring to FIG. 3 and Table 3, it showed that a thermosensitive hydrogel could be formed at a body temperature with certain mixing ratios.

Figure 4A:
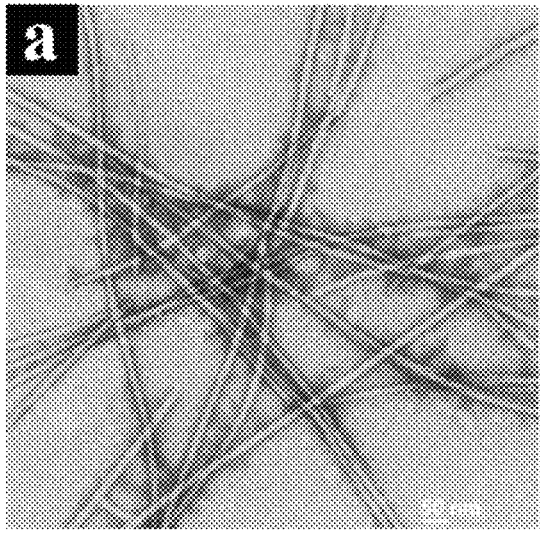
FIG. 4A was a TEM image of 0.5 wt % 5F-FF at 25° C. according to some embodiments of the invention.

In some embodiments of the invention, accordingly, in order to analyze the respective morphologies of the 5F-FF, the PEG1500 and the 5F-FF/PEG1500, and the effect of temperature changes on the morphologies, the TEM was then used to detect the 5F-FF only, the PEG1500 only and the mixture of the 5F-FF/PEG1500 at 25° C. and 37° C. The results were shown in FIGS. 4A-4F. FIGS. 4A-4F were TEM images according to some embodiments of the invention. FIG. 4A was a TEM image of 0.5 wt % 5F-FF at 25° C. according to some embodiments of the invention, FIG. 4B was a TEM image of 0.45 wt % PEG1500 at 25° C. according to some embodiments of the invention, FIG. 4C was a TEM image of a mixture of 0.5 wt % 5F-FF/0.45 wt % PEG1500 at 25° C. according to some embodiments of the invention. FIG. 4D was a TEM image of 0.5 wt % 5F-FF at 37° C. according to some embodiments of the invention, FIG. 4E was a TEM image of 0.45 wt % PEG1500 at 37° C. according to some embodiments of the invention, and FIG. 4F was a TEM image of a mixture of 0.5 wt % 5F-FF/0.45 wt % PEG1500 at 37° C. according to some embodiments of the invention.

Figure 4B:
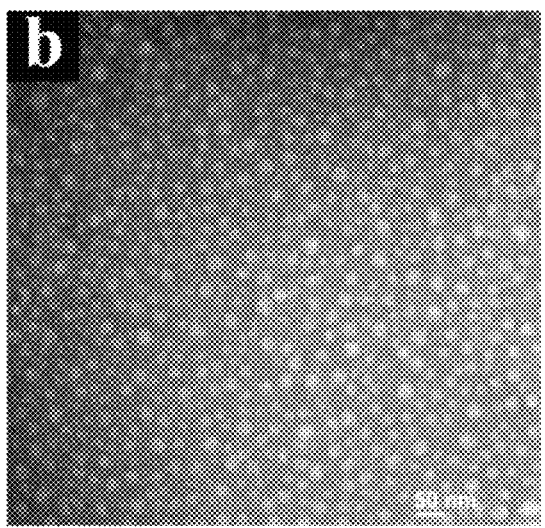
FIG. 4B was a TEM image of 0.45 wt % PEG1500 at 25° C. according to some embodiments of the invention.
Figure 4C:
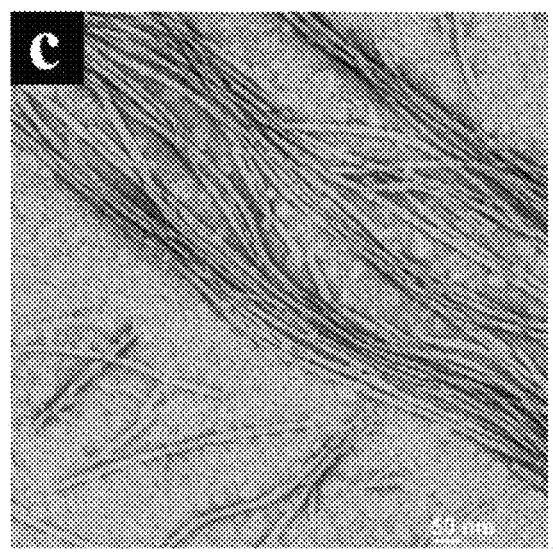
FIG. 4C was a TEM image of a mixture of 0.5 wt % 5F-FF/0.45 wt % PEG1500 at 25° C. according to some embodiments of the invention.
Figure 4C:
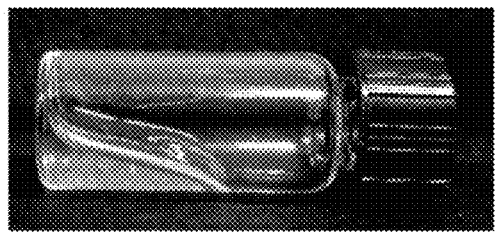
Figure 4D:
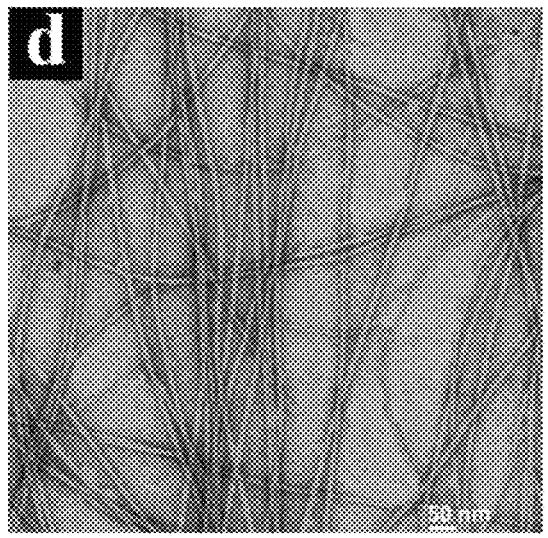
FIG. 4D was a TEM image of 0.5 wt % 5F-FF at 37° C. according to some embodiments of the invention.
Figure 4E:
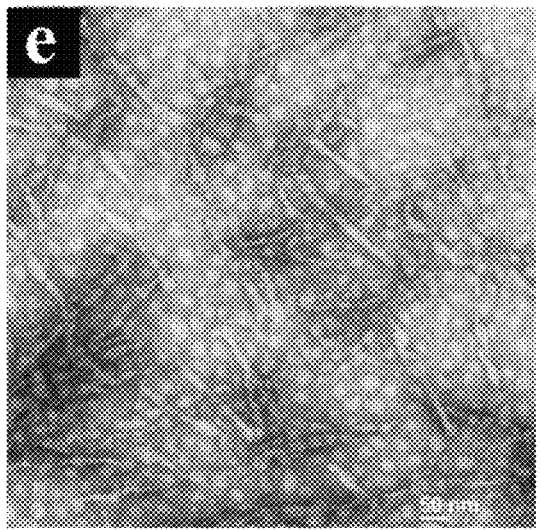
FIG. 4E was a TEM image of 0.45 wt % PEG1500 at 37° C. according to some embodiments of the invention.
Figure 4F:
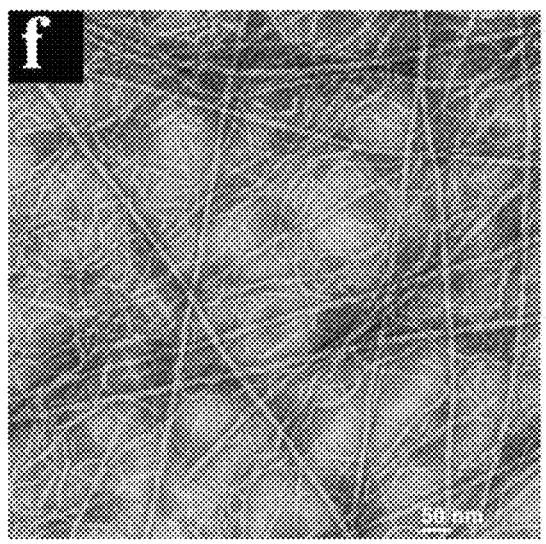
FIG. 4F was a TEM image of a mixture of 0.5 wt % 5F-FF/0.45 wt % PEG1500 at 37° C. according to some embodiments of the invention.
Figure 4F:
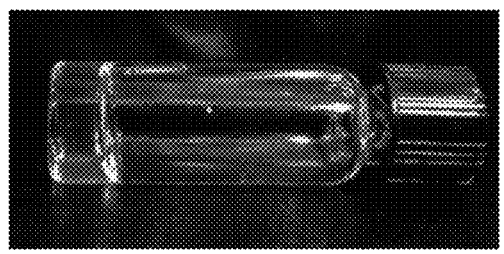
Figure 5A:
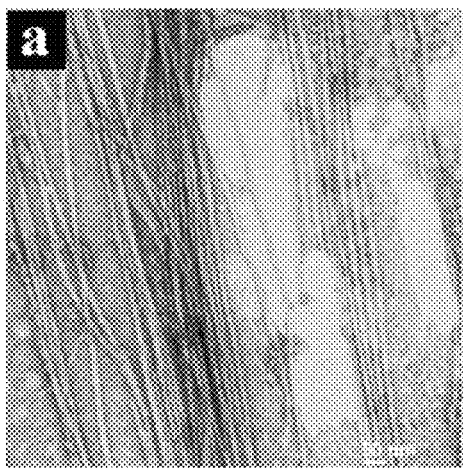
FIGS. 5A-5F were TEM images of hydrogels prepared from PEG with different molecular weights at 25° C. according to some embodiments of the invention.
Figure 5B:
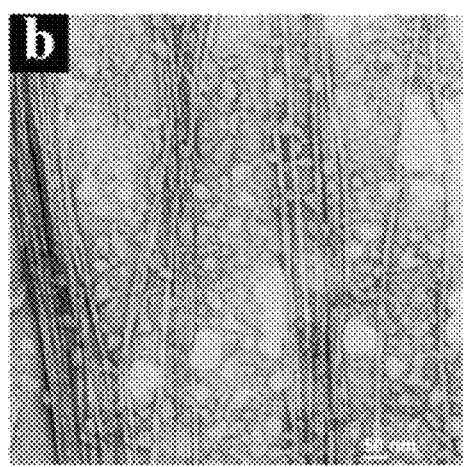
Figure 5C:
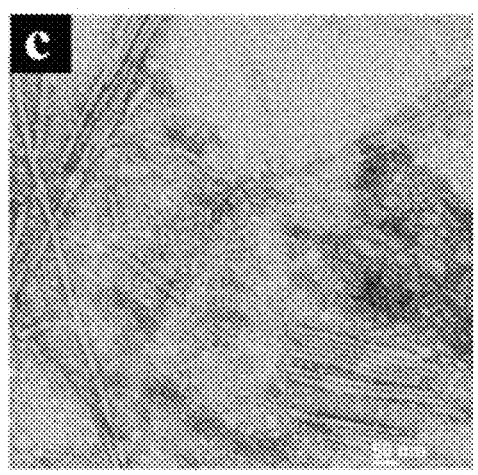
Figure 5D:
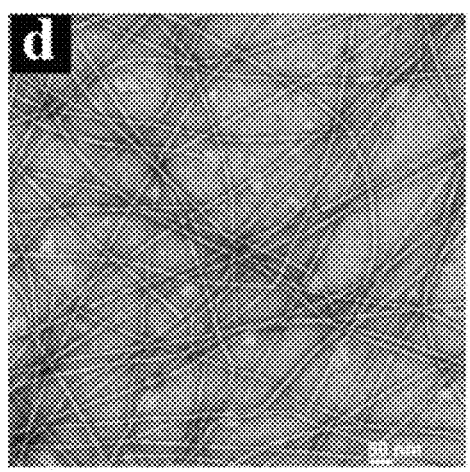
Figure 5E:
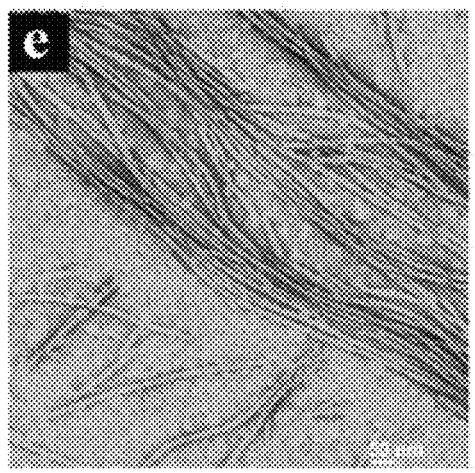
Figure 5F:
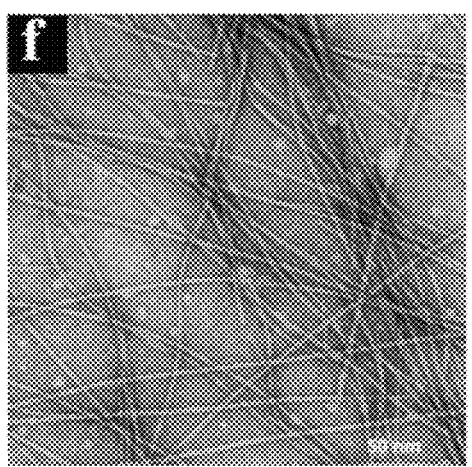
Figure 6A:
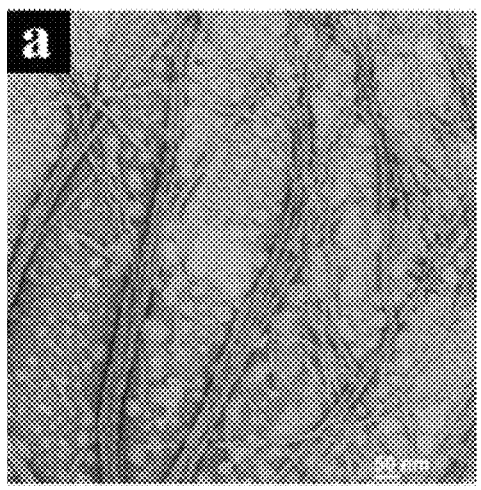
FIGS. 6A-6F were TEM images of hydrogels prepared from PEG with different molecular weights at 37° C. according to some embodiments of the invention.
Figure 6B:
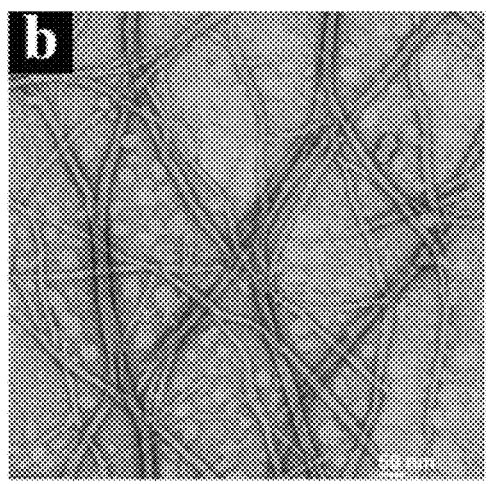
Figure 6C:
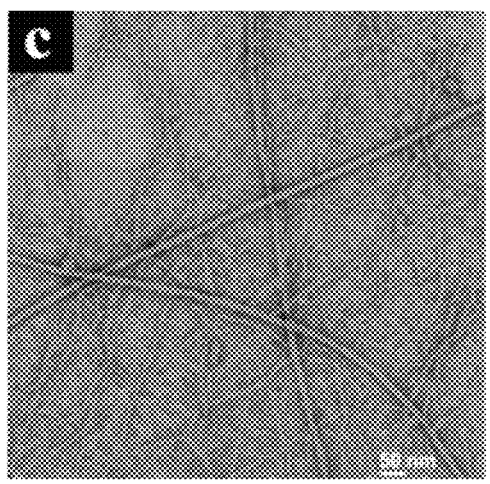
Figure 6D:
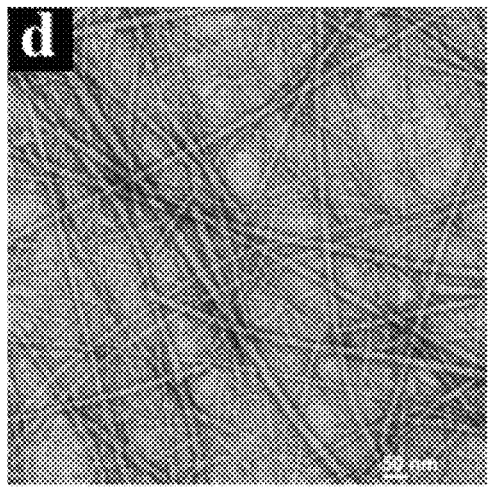
Figure 6E:
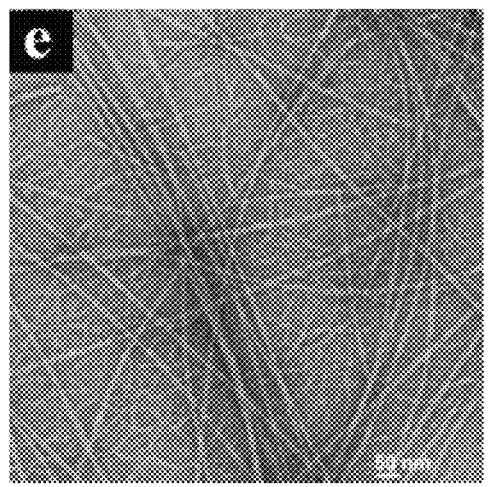
Figure 6F:
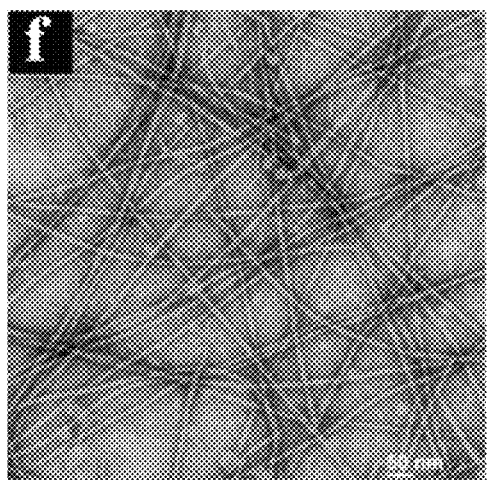

Referring to FIGS. 4A-4C, it showed that the mixture of the 5F-FF/PEG1500 was not converted into the hydrogel at 25° C. Therefore, FIG. 4A showed the fiber network from the 5F-FF, and FIG. 4B showed a nanostructure similar to the PEG1500, and FIG. 4C showed the fiber network and nanostructured particles. Referring to FIG. 4D-4F, when the temperature was raised to 37° C., a spherical nanostructure was shown to be transformed into the fiber network with a diameter of 5±1 nm, which represented that changes in temperature may aggregate the polymers into finer fiber networks. When the 5F-FF/PEG was maintained at 37° C., two different fiber network structures were shown, which were the fibers respectively from the 5F-FF of 15±1 nm in diameter, and the PEG of 5±1 nm in diameter. Therefore, it showed that 5F-FF/PEG not only had the function of a thermosensitive hydrogel, but also had a double-network (DN) fiber morphology.

In some embodiments of the invention, accordingly, in order to analyze the hierarchical mechanism of a thermosensitive DNH, the 5F-FF was mixed with the PEG of different molecular weights, and the morphologies were observed by the TEM at temperatures of 25° C. and 37° C., respectively. First, the 5F-FF/PEG mixture with a mixing ratio of 5 wt % (0.5 wt %:4.5 wt %) was selected, wherein the molecular weight of the selected PEG was 300-3000 g/mol. FIGS. 5A-5F and 6A-4F were TEM images according to some embodiments of the invention. FIGS. 5A-5F were TEM images of hydrogels prepared from PEG with different molecular weights at 25° C. according to some embodiments of the invention. FIGS. 6A-6F were TEM images of hydrogels prepared from PEG with different molecular weights at 37° C. according to some embodiments of the invention.

FIGS. 5A-5F showed that at 25° C., the 5F-FF mixed with the PEG of any molecular weight was not converted into the hydrogel. FIGS. 5A-5F accordingly showed two different fiber network structures, that is, respectively from the fiber structure of the 5F-FF and the particle structure of the PEG, which represented that the 5F-FF mixed with the PEG of any molecular weight did not form the morphology of the double-network fibers at 25° C. without any co-assembling behavior. Referring to FIGS. 6A-6F, it showed that at 37° C., the 5F-FF mixed with the PEG of any molecular weight might all form the hydrogel. Moreover, in addition to the 5F-FF/PEG300 and the 5F-FF/PEG600 of the fiber structure and the particle shape like the nanostructure, the mixture of the 5F-FF with the PEG of other molecular weights showed the DNH fiber morphology, which represented that the temperature might trigger and form the co-assembly of the thermosensitive supramolecular DN fiber hydrogel.

Figure 7:
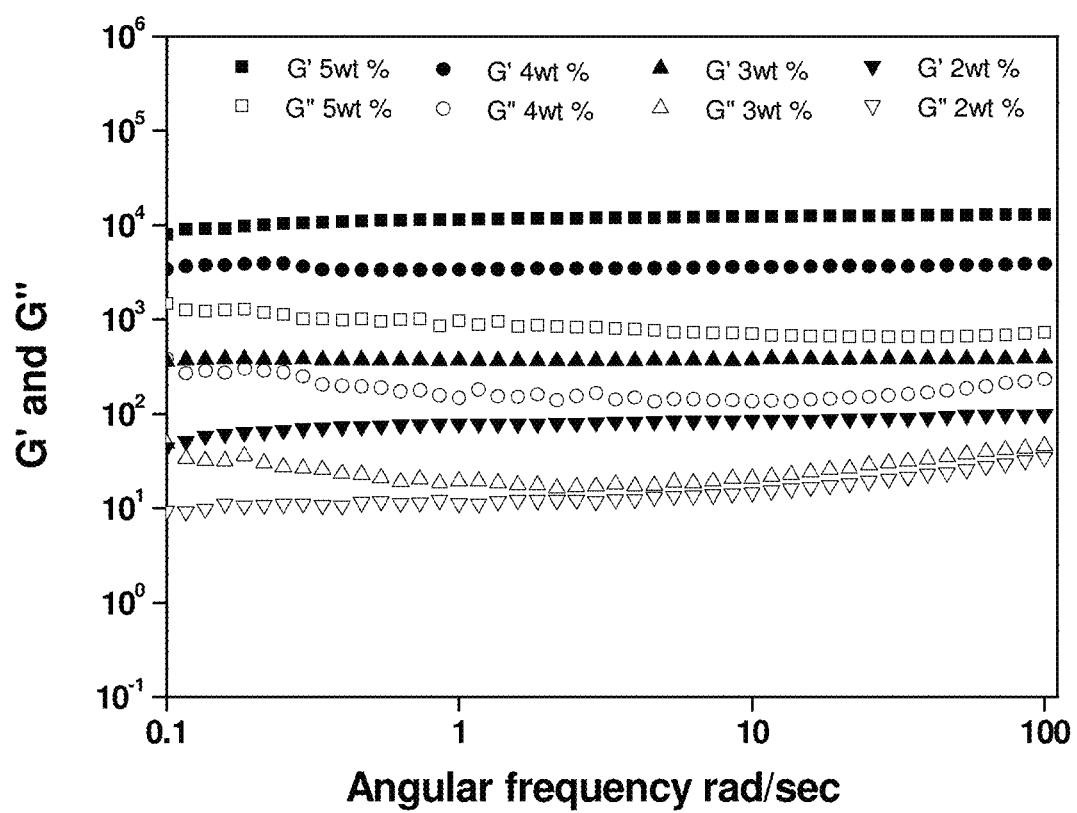
FIG. 7 was a rheological analysis chart of hydrogels 5F-FF/PEG1500 having concentrations of 2, 3, 4 and 5 wt % according to some embodiments of the invention.

In some embodiments of the invention, accordingly, with the remaining conditions the same, the 5F-FF/PEG1500 of different concentrations were subjected to the rheological tests, and the results thereof were shown in FIG. 7. The 5F-FF/PEG1500 of 2, 3, 4 and 5 wt % were selected for the tests. The chart was plotted by a G' and a G" versus a frequency sweep, wherein the G' stands for storage modulus and the G" stands for loss modulus, and the results thereof were shown in FIG. 7. FIG. 7 was a rheological analysis chart of hydrogels 5F-FF/PEG1500 having concentrations of 2, 3, 4 and 5 wt % according to some embodiments of the invention.

Referring to FIG. 7, when the 5F-FF and the PEG1500 were mixed at a mixing ratio of 2-5 wt %, the G' and the G" might be sharply increased as the temperature rises, which represented that beyond the critical temperature point, there was a solid-like behavior with greater elasticity. The values of the G' and the G" increased continuously from 30 to 50° C. till the final stage of the plateau, which represented the formation of the stable hydrogel with a certain mechanical strength. The result supported the hierarchical mechanism formed by the thermosensitive supramolecular DN fibers of the 5F-FF/PEG1500 that transformed into the stable hydrogel at 37° C.

In some embodiments of the invention, accordingly, with the remaining conditions the same, the 5F-FF mixed with the PEG of different molecular weights were subjected to the rheological tests in order to obtain an analysis of the sol-gel transition. It showed that the hydrogels composed of the PEG with a molecular weight of 300-3000 g/mol, the values of the G' and the G" increase as the temperature increases, which represented that the hydrogels composed of the PEG with different molecular weights also had the properties of the thermosensitive supramolecular hydrogel.

In some embodiments of the invention, in order to analyze the reversibility of the hydrogel, after the sample was cooled to the initial temperature, a second temperature scan of the G' and the G" was performed. It showed that the results of the two measurements were almost overlapped, which represented that the sol-gel transition was reversible. In addition, a 5F-FF/PEG1500 solution of 5 wt % forms a free-standing transparent hydrogel near 37° C. of the body temperature and returns to a free-floating fluid when cooled to 0° C. The sol-gel transition was rapid and a stable hydrogel could be formed in less than 15 minutes. In some embodiments of the invention, the sol-gel transition was proven to be completely reversible by experiments of heating and cooling repeatedly.

Figure 8A:
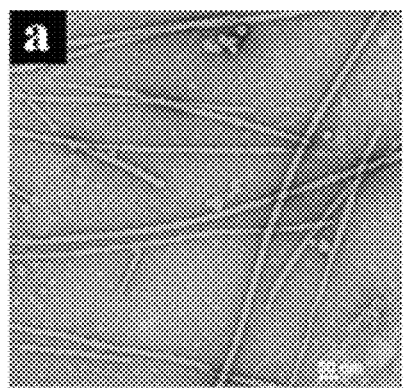
FIG. 8A was a TEM image of a solution of 5F-FF/PEG1500 at 25° C. according to some embodiments of the invention.
Figure 8B:
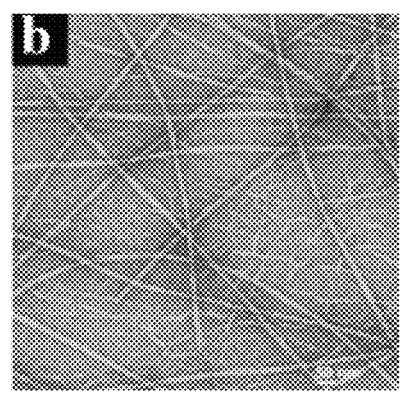
FIG. 8B was a TEM image of a hydrogel 5F-FF/PEG1500 at 37° C. according to some embodiments of the invention.
Figure 8C:
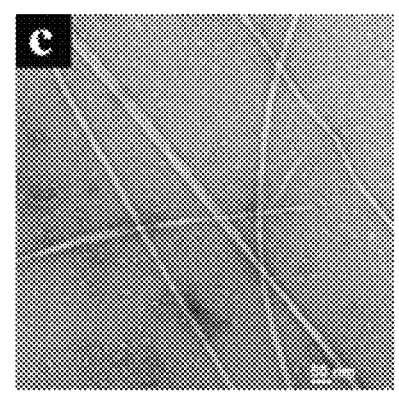
FIG. 8C was a TEM image of a solution of 5F-FF/PEG1500 at 0° C. according to some embodiments of the invention.
Figure 8D:
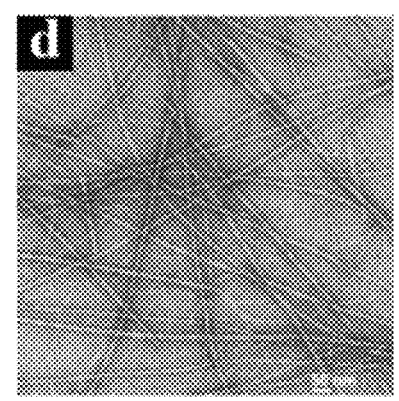
FIG. 8D was a TEM image of a hydrogel 5F-FF/PEG1500 hydrogel at 37° C. according to some embodiments of the invention.

In some embodiments of the invention, accordingly, with the remaining conditions the same, the sol-gel transition was analyzed by the TEM, and the temperature was increased and decreased repeatedly to analyze the morphology of the hydrogel, wherein the results were shown in FIGS. 8A-8D. FIG. 8A was a TEM image of a solution of 5F-FF/PEG1500 at 25° C. according to some embodiments of the invention, FIG. 8B was a TEM image of a hydrogel 5F-FF/PEG1500 at 37° C. according to some embodiments of the invention, FIG. 8C was a TEM image of a solution of 5F-FF/PEG1500 at 0° C. according to some embodiments of the invention, and FIG. 8D was a TEM image of a hydrogel 5F-FF/PEG1500 hydrogel at 37° C. according to some embodiments of the invention.

Referring to FIGS. 8A-8D, it showed that no DN fiber was formed at 25° C., and when the temperature rises to 37° C., the 5F-FF/PEG1500 was completely transformed into a DN fiber shape like the nanostructure. That is, the sol-gel transition of the hydrogel according to some embodiments of the invention was indeed reversible.

In some embodiments of the invention, accordingly, with the remaining conditions the same, the PEG of different molecular weights was selected and mixed with the 5F-FF to analyze the characteristics of the time-dependency, wherein the mixing ratio and the results thereof were shown in Table 4.

TABLE 4

| Samples | pH | Time $T_{sol-gel}$ (min) | Morphology image of the TEM |
| --- | --- | --- | --- |
| 5F-FF only | 7.0 | Gel | Single fiber, length ±15 nm |
| 5F-FF/PEG300 | 7.0 | 90 | 5F-FF fiber ±15 nm PEG spherical ±5 nm |
| 5F-FF/PEG600 | 7.0 | 60 | 5F-FF fiber ±15 nm PEG spherical ±5 nm |
| 5F-FF/PEG1000 | 7.0 | 45 | Double fiber 5F-FF ±15 nm PEG ±5 nm |
| 5F-FF/PEG1500 | 7.0 | 30 | Double fiber 5F-FF ±15 nm PEG ±5 nm |
| 5F-FF/PEG2000 | 7.0 | 30 | Double fiber 5F-FF ±15 nm PEG ±5 nm |
| 5F-FF/PEG3000 | 7.0 | 30 | Double fiber 5F-FF ±15 nm PEG ±5 nm |

Referring to Table 4, it showed that the 5F-FF/PEG300 undergoes the thermosensitive gelation after 90 minutes, the 5F-FF/PEG600 and the 5F-FF/PEG1000 undergo the thermosensitive gelation after 60 minutes and 45 minutes, respectively, and the 5F-FF/PEG1500, the 5F-FF/PEG2000 and the 5F-FF/PEG3000 all undergo the thermosensitive gelation after 30 minutes. It showed that the 5F-FF/PEG300 and the 5F-FF/PEG600 require the longest time to form the gel at 37° C., which might be one of the reason that the 5F-FF/PEG300 and the 5F-FF/PEG600 do not form the complete DN fiber. In addition, when the 5F-FF/PEG1500 was maintained at 37° C., the TEM image thereof showed that with the 5F-FF/PEG1500 still in a solution phase after 5 minutes at 37° C., there were two different networks existing, that is, the fibers and the particles like the nanostructure. After 15 minutes, the 5F-FF/PEG converted into the hydrogel and was already in the form of the DNH fiber. The stable hydrogel was completely formed within 30 minutes, wherein the long and wide fibers with an average diameter of 15 nm were used as the first network from the 5F-FF, and the long and thin fibers with an average diameter of 5 nm were used as the second network from the PEG.

Figure 9A:
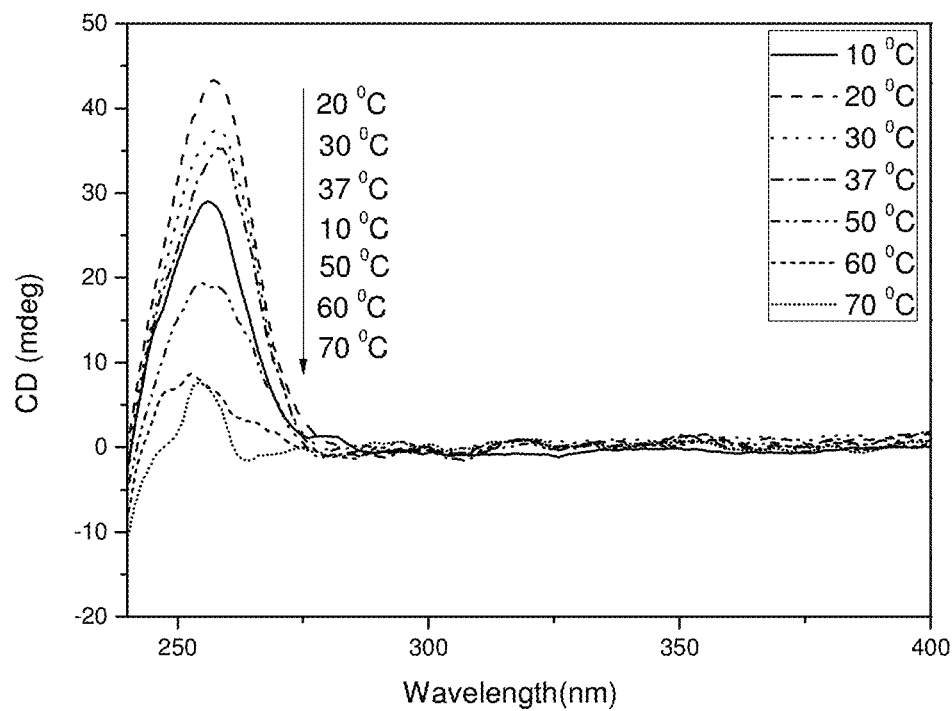
FIG. 9A was a diagram showing circular dichroism spectrum (CD) of 0.5 wt % 5F-FF according to some embodiments of the invention where the solvent is water.
Figure 9B:
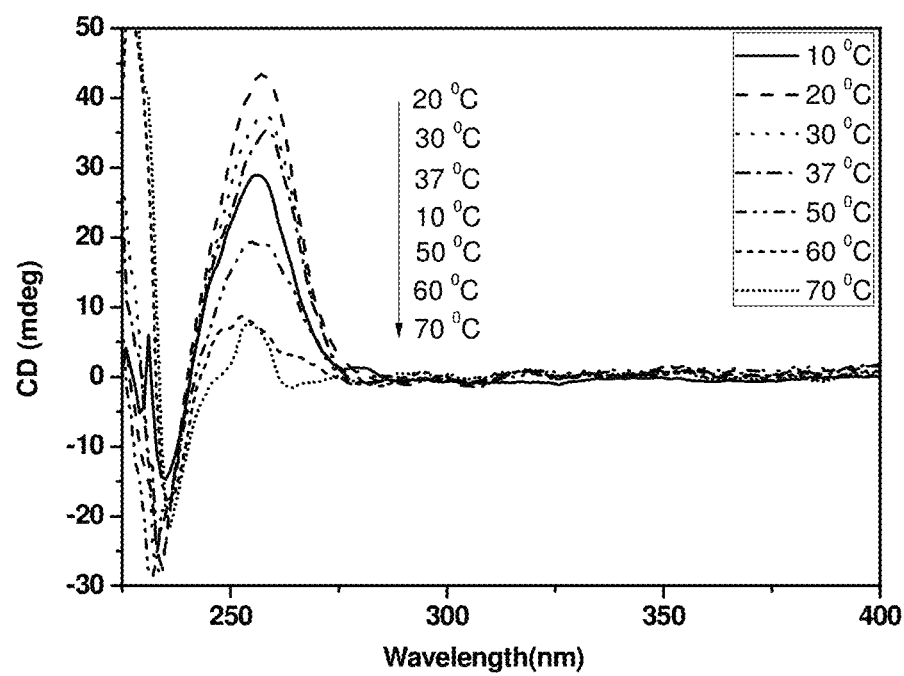
FIG. 9B was a diagram showing CD spectrum of 0.5 wt % 5F-FF/PEG1500 according to some embodiments of the invention where the solvent is water.
Figure 9C:
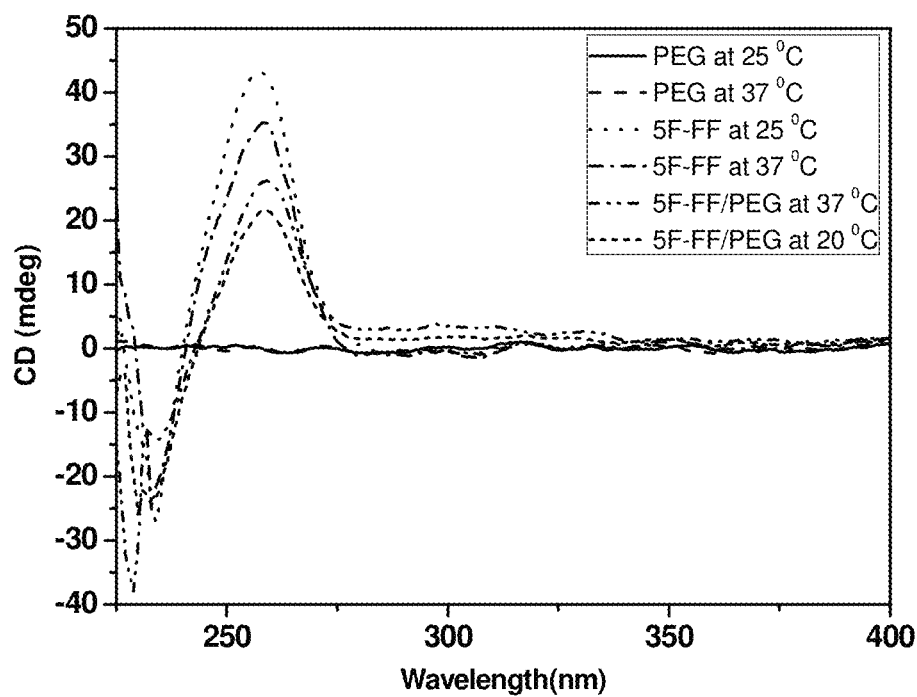
FIG. 9C was a diagram showing CD spectrum of 5F-FF, PEG1500 and 5F-FF/PEG according to some embodiments of the invention where the solvent is water.
Figure 9D:
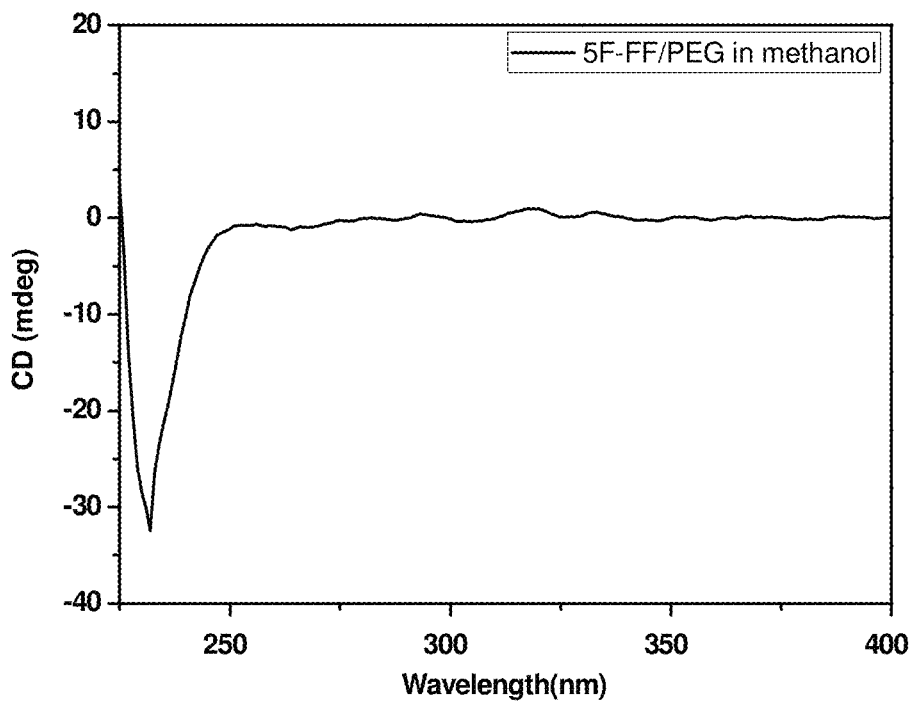
FIG. 9D was a diagram showing CD spectrum of 5 wt % 5F-FF/PEG1500 according to some embodiments of the invention where the solvent is methanol.

In some embodiments of the invention, accordingly, the circular dichroism (abbreviated as CD) was used for analyzing. The 5F-FF, the PEG1500 and the 5F-FF/PEG were selected, and the results thereof were shown in FIGS. 9A-9D. FIG. 9A was a diagram showing circular dichroism spectrum (CD) of 0.5 wt % 5F-FF according to some embodiments of the invention where the solvent was water, FIG. 9B was a diagram showing CD spectrum of 0.5 wt % 5F-FF/PEG1500 according to some embodiments of the invention where the solvent was water, FIG. 9C was a diagram showing CD spectrum of 5F-FF, PEG1500 and 5F-FF/PEG according to some embodiments of the invention where the solvent was water, and FIG. 9D was a diagram showing CD spectrum of 5 wt % 5F-FF/PEG1500 according to some embodiments of the invention where the solvent was methanol.

As shown in FIGS. 9A-9D, the 0.5 wt % 5F-FF hydrogel showed a strong positive signal at 260 nm. The Cotton effect (interaction between 7-7 bonds) at 260 nm showed an arrangement formed by pentafluoroenyl groups in the state of the hydrogel, and the chiral structure formed by diphenylalanine accurately induce the CD signal at 260 nm. In addition, the peaks in the range of 215-240 nm showed the possibilities of forming a β-sheet and/or β-turn structure. Although no extensive hydrogen-bonding interaction of the 5F-FF was observed, a peak of a dimer was found in the mass spectrum. In addition, it showed that the cooperative effect of an aromatic-aromatic and hydrogen-bond interactions might be the essential driving force to form the self-assembled/co-assembly nanofibers and hydrogels. Meanwhile, a pure PEG1500 with any concentration did not show any peaks in the CD spectrum. However, by mixing the 5F-FF and the PEG1500, not only a positive Cotton effect peak might exist at 260 nm, but also β-sheet might exist near 214-240 nm, and the signal was already close to the baseline.

Figure 10:
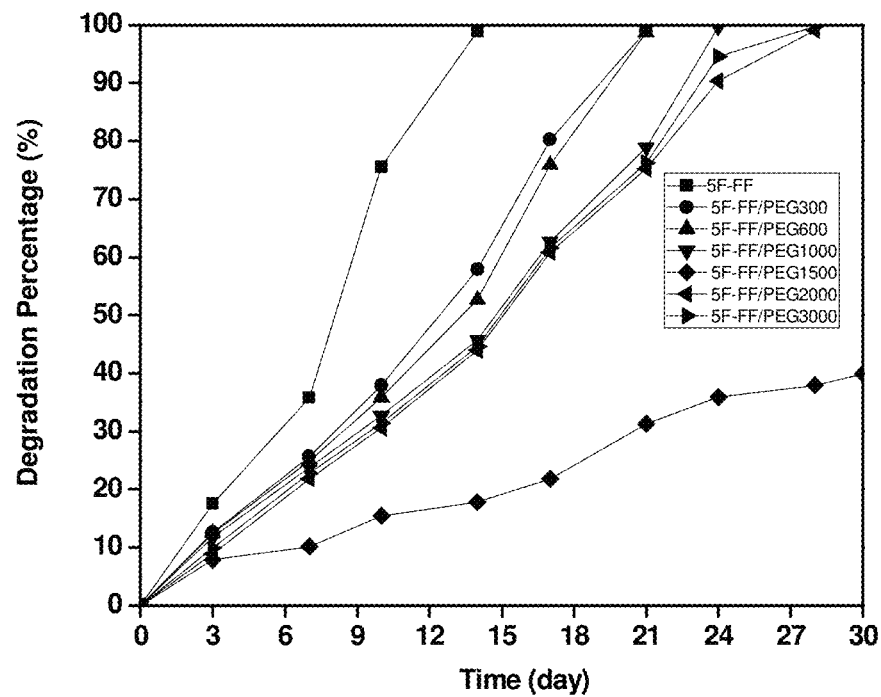
FIG. 10 was a diagram showing specific degradation percentage over time of the 5F-FF, 5F-FF/PEG300, 5F-FF/PEG600, 5F-FF/PEG1000, 5F-FF/PEG1500, 5F-FF/PEG2000, and 5F-FF/PEG3000 alone in the PBS according to some embodiments of the invention.

In some embodiments of the invention, accordingly, with the remaining conditions the same, the stability of the thermosensitive hydrogel was tested by immersing the samples into a PBS with the pH value of 7.4 at 37° C., and the result thereof was shown in FIG. 10. FIG. 10 was a diagram showing specific degradation percentage over time of the 5F-FF, 5F-FF/PEG300, 5F-FF/PEG600, 5F-FF/

PEG1000, 5F-FF/PEG1500, 5F-FF/PEG2000, and 5F-FF/PEG3000 alone in the PBS according to some embodiments of the invention.

Referring to FIG. 10, it showed that on the seventh day, the degradation percentages of the 5F-FF, the 5F-FF/PEG300, the 5F-FF/PEG600, the 5F-FF/PEG1000, the 5F-FF/PEG1500, the 5F-FF/PEG2000 and the 5F-FF/PEG3000 hydrogels were 35.75%, 25.65%, 24.86%, 23.76%, 10.12%, 21.85%, and 22.75%, respectively. The 5F-FF only was completely dissolved within 14 days compared to day 0 due to the weak non-covalent interaction force between the 5F-FF molecules. It was well known that a salt has little effect on the stability of the peptide hydrogel. In addition, on day 21, the 5F-FF/PEG300 and the 5F-FF/PEG600 were completely dissolved; on day 24, the 5F-FF/PEG1000 was completely dissolved; and on day 28, the 5F-FF/PEG2000 and the 5F-FF/PEG3000 were completely dissolved. However, after 30 days, the 5F-FF/PEG1500 was still in a hydrogel state, which represented that the stability of the 5F-FF/PEG1500 hydrogel was greater than the other hydrogels. The 5F-FF/PEG1500 hydrogel slowly degraded after cultured in 30 days, and a degradation rate of 39.89% thereof after 4 weeks was reached. The stability represented that the 5F-FF/PEG1500 had a sufficient duration and a good performance for biological applications, such as the application to a nucleus pulposus (NP) cells of an extracellular matrix (ECM) in regenerative cells.

Figure 11:
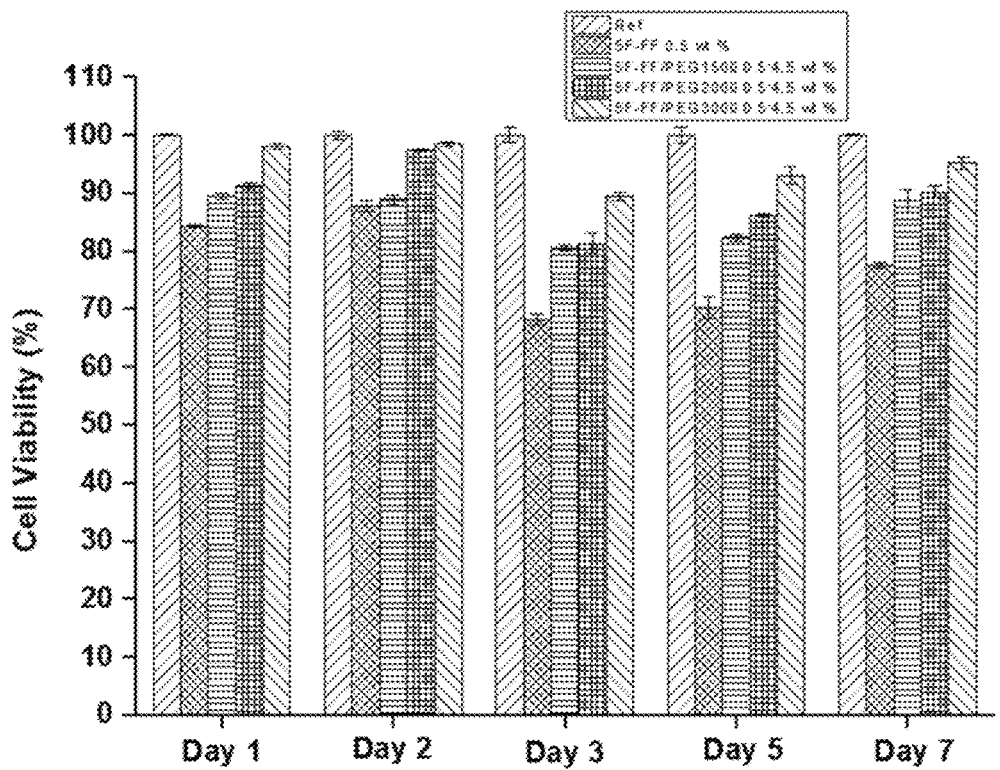
FIG. 11 was a diagram showing cell viability of cells treated with 0.5 wt % 5F-FF, 0.5 wt %: 4.5 wt % 5F-FF/PEG1500, 0.5 wt %: 4.5 wt % 5F-FF/PEG2000 and 0.5 wt %: 4.5 wt % 5F-FF/PEG3000 according to some embodiments of the invention.

In some embodiments of the invention, a cell viability test (MTT assay) was used for a colorimetric assay to analyze the biocompatibilities of the samples. In detail, a 0.5 wt % 5F-FF, a 0.5 wt %: 4.5 wt % 5F-FF/PEG1500, a 0.5 wt %: 4.5 wt % 5F-FF/PEG2000, and a 0.5 wt %: 4.5 wt % 5F-FF/PEG3000 (hydrogels under neutral conditions), and the immortalized human mesenchymal stem cells (hMSC, 3a6) was selected for testing, wherein the results were shown in FIG. 11. FIG. 11 was a diagram showing cell viability of cells treated with 0.5 wt % 5F-FF, 0.5 wt %: 4.5 wt % 5F-FF/PEG1500, 0.5 wt %: 4.5 wt % 5F-FF/PEG2000 and 0.5 wt %: 4.5 wt % 5F-FF/PEG3000 according to some embodiments of the invention.

Referring to FIG. 11, it showed that the cells all had a high survival rate within 7 days. The survival rate of the 0.5 wt % 5F-FF was 84.01% on day 1, 88.58% on day 2, 68.17% on day 3, 73.33% on day 5, and 84.05% on day 7. It was assumed that the initial cell survival rate could be enhanced by combining peptide molecules with the PEG, so the PEG with different molecular weights was mixed with the 5F-FF. As shown in the FIG. 11, the survival rate of the 0.5 wt %: 4.5 wt % 5F-FF/PEG1500 was 89.42% on day 1, 88.87% on day 2, 80.45% on day 3, 82.29% on day 5, and 88.68% on day 7. The survival rate of the 0.5 wt %: 4.5 wt % 5F-FF/PEG2000 was increased to 91.20% on day 1, 97.31% on day 2, 81.32% on day 3, 86.15% on day 5, and 90.18% on day 7. In addition, the survival rate of the 0.5 wt %: 4.5 wt % 5F-FF/PEG3000 was increased to 98.13% on day 1, 98.51% on day 2, 89.50% on day 3, 92.98% on day 5, and 95.25% on day 7. The above represented the half inhibitory concentrations ($IC_{50}$) of the 0.5 wt %: 4.5 wt % 5F-FF/PEG1500, the 0.5 wt %: 4.5 wt % 5F-FF/PEG2000, and the 0.5 wt %: 4.5 wt % 5F-FF/PEG3000 were high with the survival rates higher than 80%, so they were all biocompatible.

In some embodiments of the invention, with the remaining conditions the same, different peptide molecules were selected and mixed with the PEG1500 in order to measure the time required for the gelation at 37° C., wherein the mixing ratio and the results thereof were shown in Table 5.

TABLE 5

| Samples | pH | CGC (wt %) | Time $T_{sol-gel}$ (hr) | Diameter of fiber (nm) |
|---|---|---|---|---|
| 0F-FF | 7.0 | — | — | 15 ± 1 |
| 0F-FF/PEG1500 | 7.0 | 1 | 3 | 15 ± 1 |
|  |  |  |  | 5 ± 1 |
| 1F-FF | 7.0 | 1 | — | 10 ± 5 |
| 1F-FF/PEG1500 | 7.0 | 1 | 2 | 10 ± 1 |
|  |  |  |  | 5 ± 1 |
| 3F-FF | 7.0 | 0.5 | — | 11 ± 5 |
| 3F-FF/PEG1500 | 7.0 | 0.5 | 2 | 11 ± 1 |
|  |  |  |  | 5 ± 1 |

Referring to Table 5, it showed that the time required for the gelation of different types of the peptide molecules varied greatly, which represented that the total number of fluorine on the benzene ring of the peptide molecules might strongly affect the co-assembly rate. It showed that the thermosensitive hydrogel was formed by the co-assembly of supramolecular double-network fibers. At 25° C., the 0F-FF/PEG1500, the 1F-FF/PEG1500 and the 3F-FF/PEG1500 were still the solutions, and the 0F-FF/PEG1500, the 1F-FF/PEG1500 and the 3F-FF/PEG1500 were the hydrogels at 37° C. At 25° C., the fibrous nanostructures from the 1F-FF or the 3F-FF, and the particle structures from the PEG were shown, which represented that the formation of the DN fiber hydrogels had not performed yet, and the co-assembling behavior could not be further confirmed. However, when the temperature was raised to 37° C., the 0F-FF/PEG1500, the 1F-FF/PEG1500 and the 3F-FF/PEG1500 were shown to be the stable hydrogels.

Figure 12A:
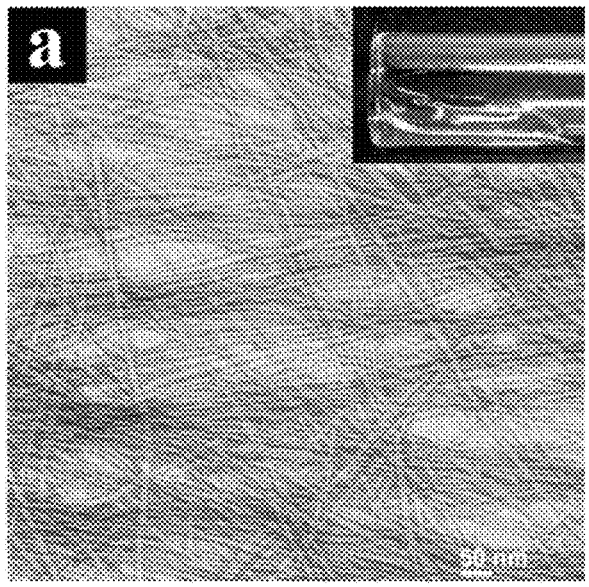
FIG. 12A was a TEM image of a solution of 0.5 wt % 1F-FF according to an embodiment of the invention.
Figure 12B:
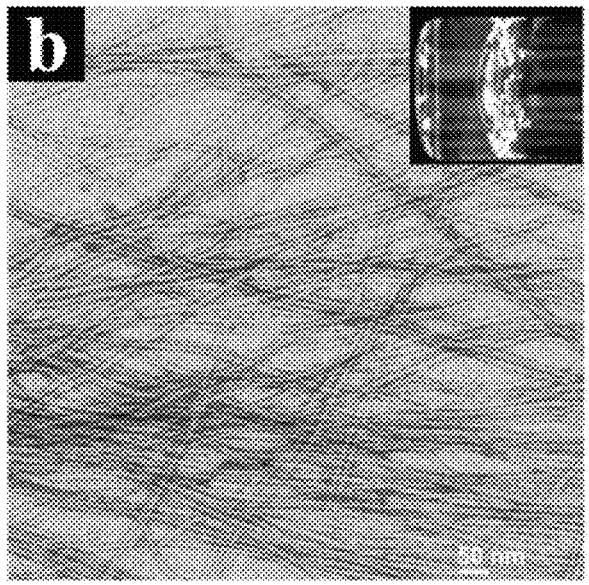
FIG. 12B was a TEM image of a hydrogel 1 wt % 1F-FF according to an embodiment of the invention.

In some embodiments of the invention, accordingly, the 1F-FF-PEG1500 of different mixing ratios at 37° C. were analyzed for the co-assembly by the TEM, and the results thereof were shown in FIGS. 12A-12D. FIG. 12A was a TEM image of a solution of 0.5 wt % 1F-FF according to an embodiment of the invention, FIG. 12B was a TEM image of a hydrogel 1 wt % 1F-FF according to an embodiment of the invention, FIG. 12C was a TEM image of a solution of 0.5 wt %: 4.5 wt % 1F-FF/PEG1500 according to an embodiment of the invention, and FIG. 12D was a TEM image of a solution of 1 wt %: 4 wt % 1F-FF/PEG1500 according to an embodiment of the invention.

Figure 12C:
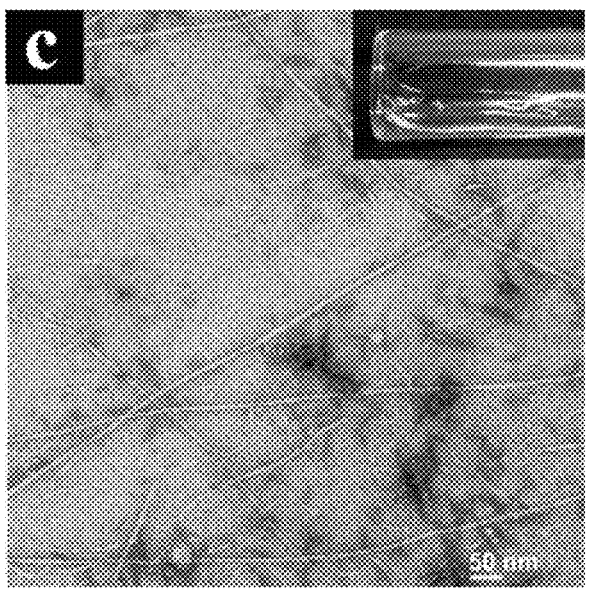
FIG. 12C was a TEM image of a solution of 0.5 wt %: 4.5 wt % 1F-FF/PEG1500 according to an embodiment of the invention.
Figure 12D:
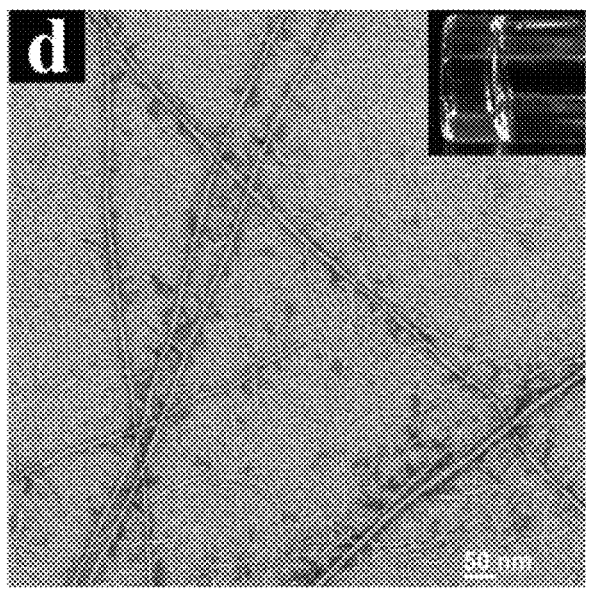
FIG. 12D was a TEM image of a solution of 1 wt %: 4 wt % 1F-FF/PEG1500 according to an embodiment of the invention.
Figure 13A:
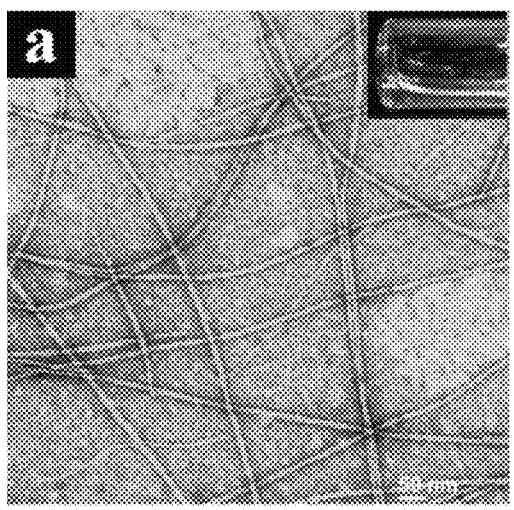
FIGS. 13A-13F were TEM images of a solution of 0.5 wt %: 4.5 wt % 3F-FF/PEG1500 according to some embodiments of the invention.
Figure 13B:
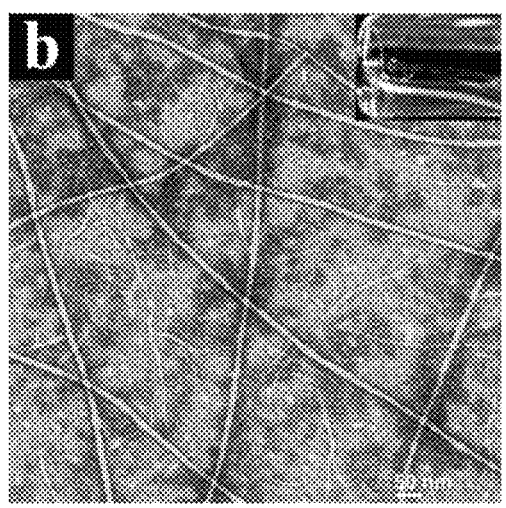
Figure 13C:
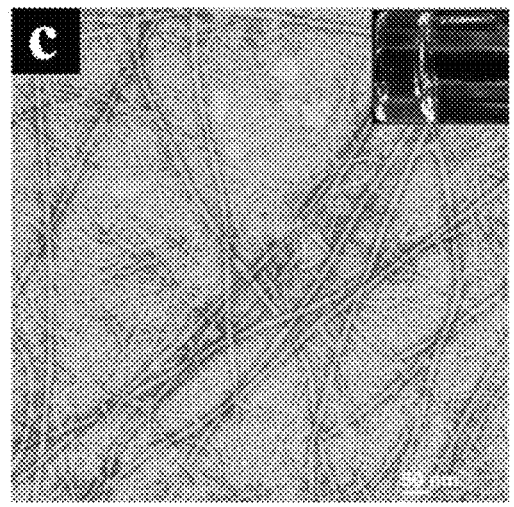
Figure 13D:
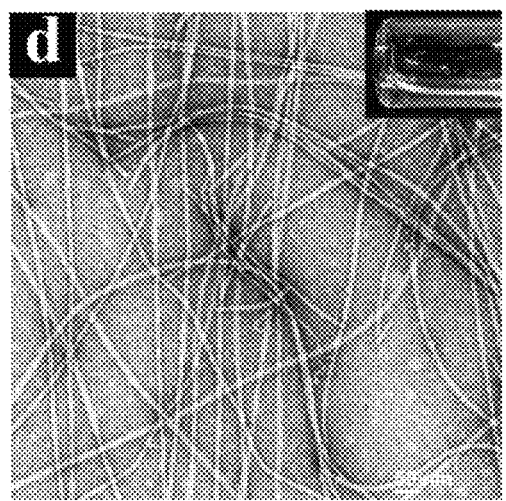
Figure 13E:
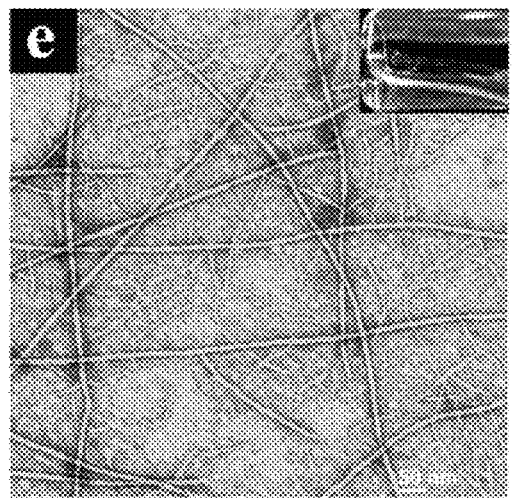
Figure 13F:
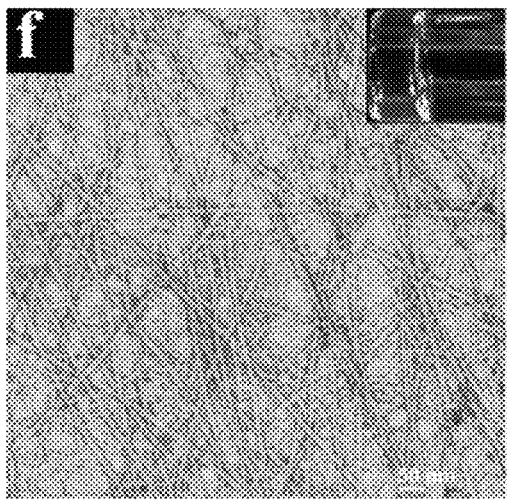

Referring to FIGS. 12C-12D, it showed that the 1F-FF/PEG1500 was a self-assembled fiber hydrogel. The above represented that the derivatives of fluorine could be effectively copolymerized with the PEG to form a double-network hydrogel fiber, so the perfluorination of the phenyl side chain did not need to be used for facilitating an efficient co-assembly with the polyethylene glycol. In other words, the above supported the physical interaction between the peptide molecules and the polymers, that is, intermolecular hydrogen bonding was the reason for facilitating the beneficial non-covalent effect of the co-assembly.

Figure 14A:
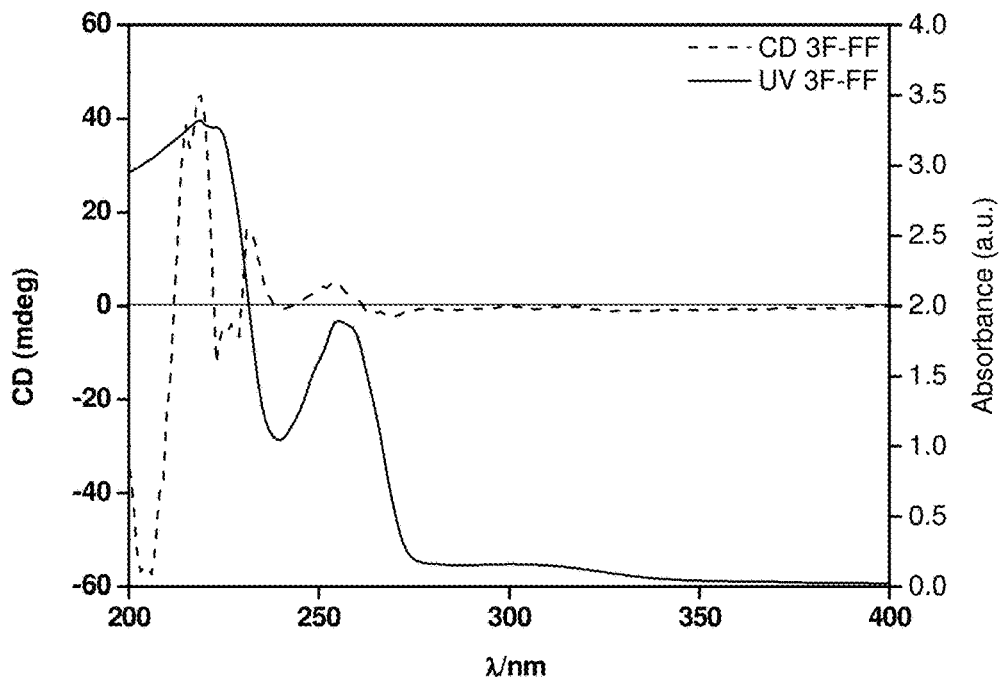
FIG. 14A was a diagram showing CD and ultraviolet-visible (UV-Vis) light spectrum of a hydrogel 0.5 wt % 3F-FF according to some embodiments of the invention.
Figure 14B:
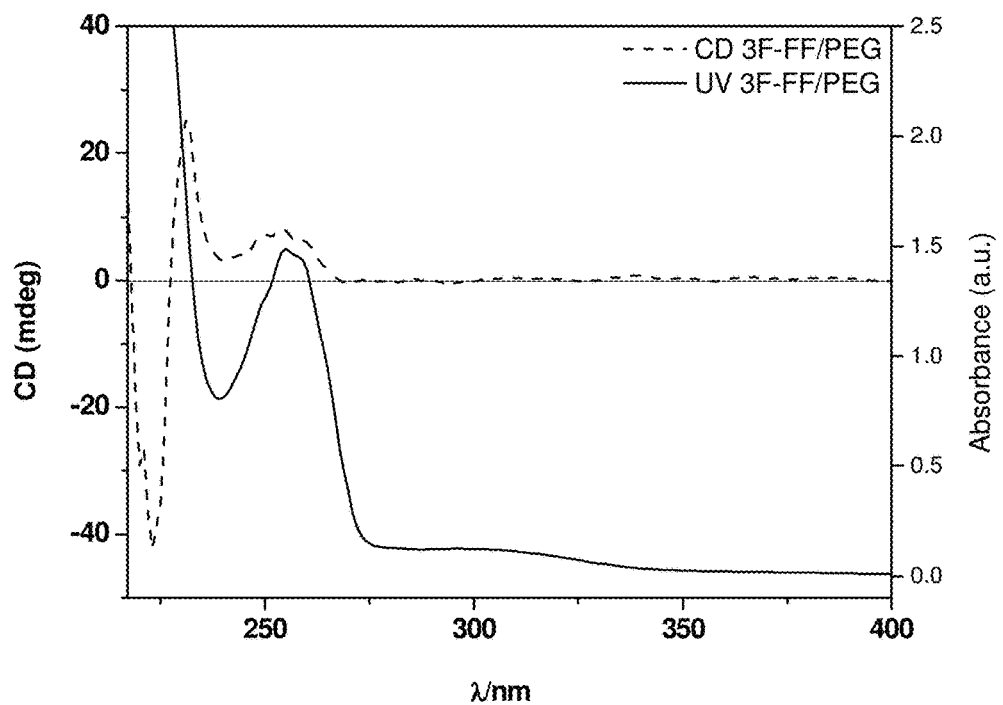
FIG. 14B was a diagram showing CD and UV-Vis spectrum of a solution of 0.5 wt %: 4.5 wt % 3F-FF/PEG according to some embodiments of the invention.

FIGS. 13A-13F were TEM images of a solution of 0.5 wt %: 4.5 wt % 3F-FF/PEG1500 according to some embodiments of the invention. Accordingly, in some embodiments of the invention, the remaining conditions were the same. As shown in FIGS. 14A-14B and 15A-15B, the CD and ultraviolet-visible light spectrum (UV-vis) were used for analysis, respectively. FIG. 14A was a diagram showing CD and ultraviolet-visible (UV-Vis) light spectrum of a hydrogel 0.5 wt % 3F-FF according to some embodiments of the invention, FIG. 14B was a diagram showing CD and UV-Vis spectrum of a solution of 0.5 wt %: 4.5 wt % 3F-FF/PEG according to some embodiments of the invention, FIG. 15A was a diagram showing CD and UV-Vis spectrum of a hydrogel 0.5 wt % 1F-FF according to some embodiments of the invention, and FIG. 15B was a diagram showing CD and UV-Vis spectrum of a solution of 0.5 wt %: 4.5 wt % 1F-FF/PEG according to some embodiments of the invention.

Figure 15A:
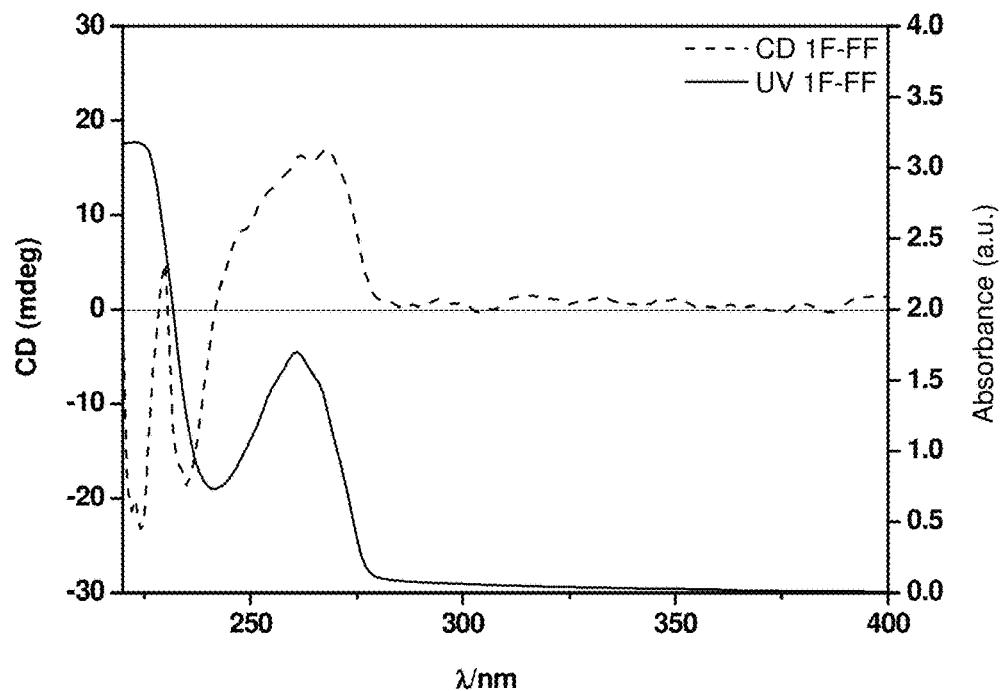
FIG. 15A was a diagram showing CD and UV-Vis spectrum of a hydrogel 0.5 wt % 1F-FF according to some embodiments of the invention.
Figure 15B:
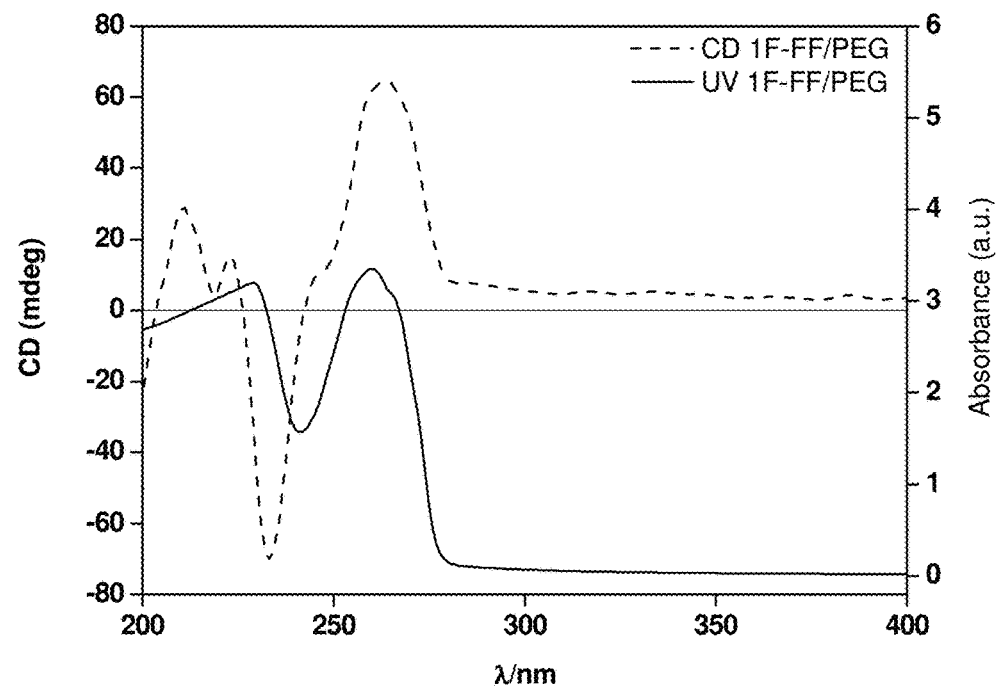
FIG. 15B was a diagram showing CD and UV-Vis spectrum of a solution of 0.5 wt %: 4.5 wt % 1F-FF/PEG according to some embodiments of the invention.

Referring to FIGS. 15A-15B, it showed that the co-assembly rate (defined as the time required to change from a transparent solution to a transparent hydrogel at 37° C.) showed a dependency on the total number of fluorine in the fluorinated peptide molecule. The 3F-FF/PEG1500 and the 1F-FF/PEG1500 not only showed the positive Cotton effect peaks at 254 nm, but also showed the 3-fold plates at 214-240 nm, and the signals were close to and above the baseline.

Figure 16A:
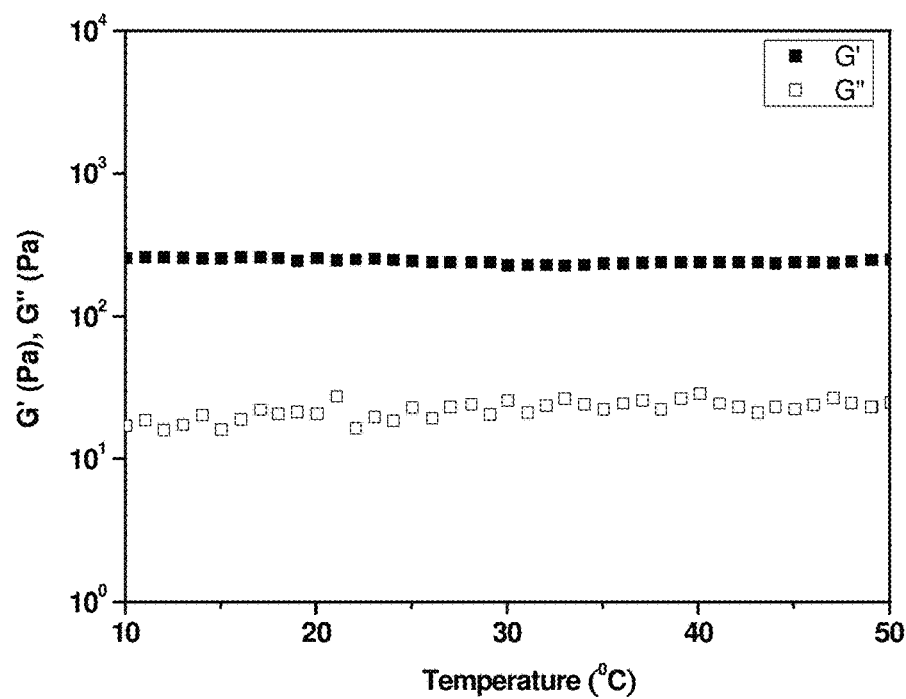
FIG. 16A was a diagram showing rheological behavior of a hydrogel 0.5 wt % 3F-FF according to some embodiments of the invention.
Figure 16B:
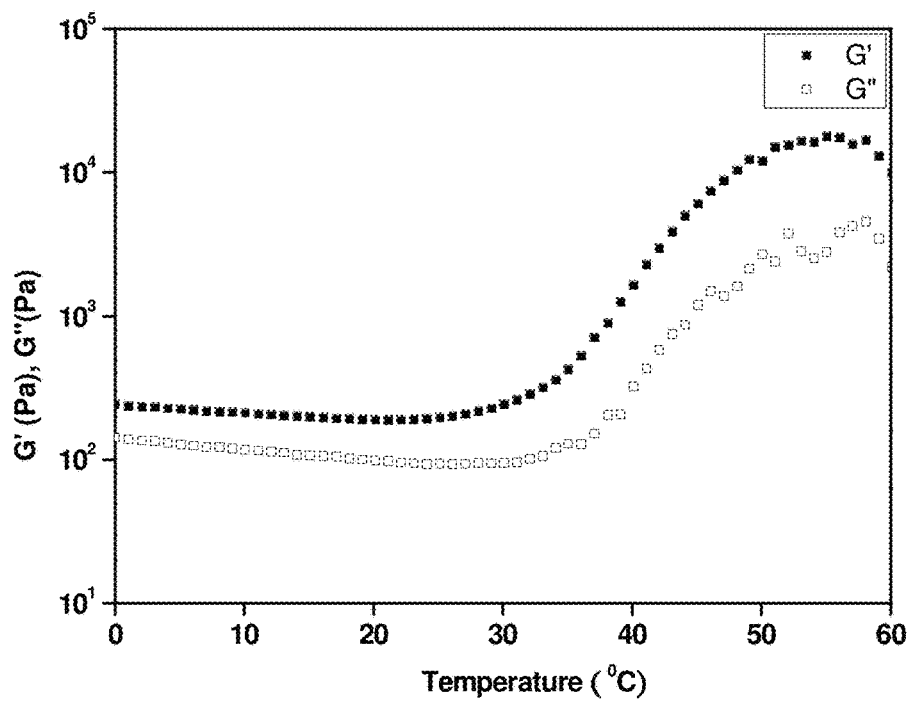
FIG. 16B was a diagram showing rheological behavior of a solution of 0.5 wt %: 4.5 wt % 3F-FF/PEG according to some embodiments of the invention.
Figure 17A:
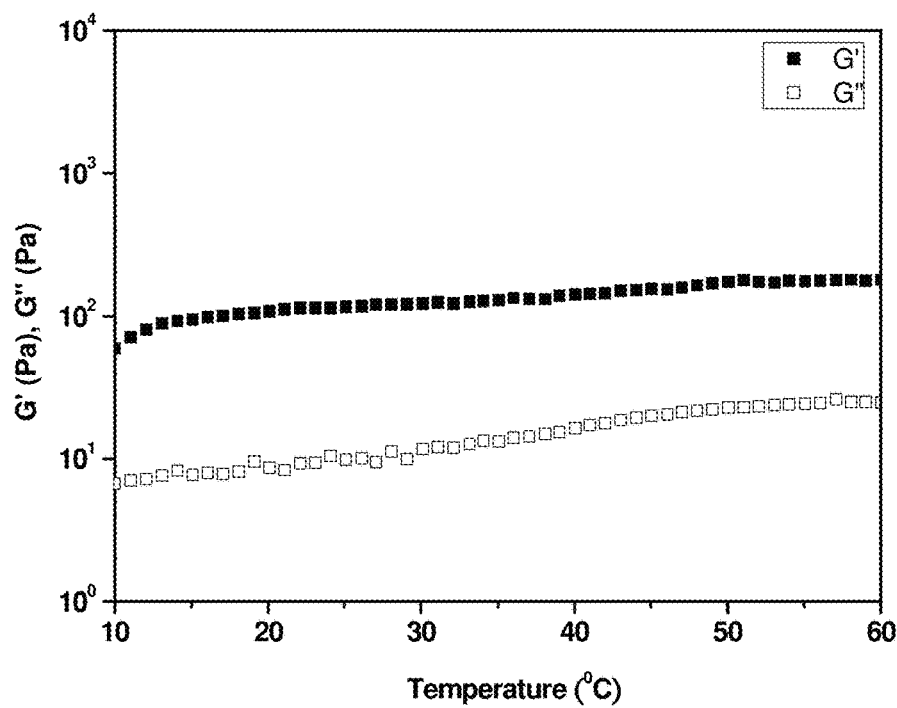
FIG. 17A was a diagram showing rheological behavior of a hydrogel 0.5 wt % 1F-FF according to some embodiments of the invention.
Figure 17B:
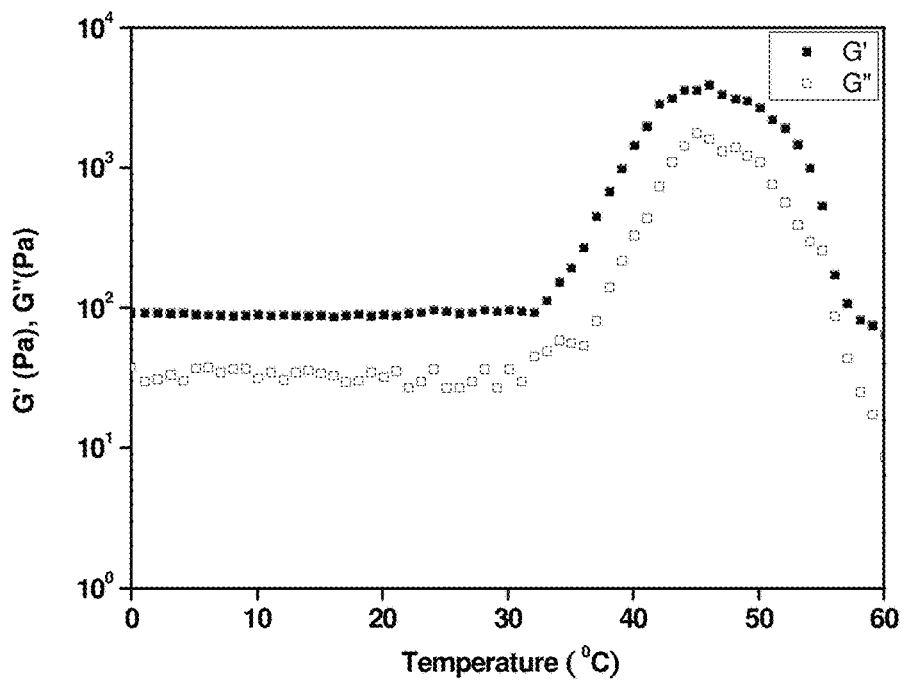
FIG. 17B was a diagram showing rheological behavior of a solution of 1 wt %: 4 wt % 1F-FF/PEG according to some embodiments of the invention.
Figure 18A:
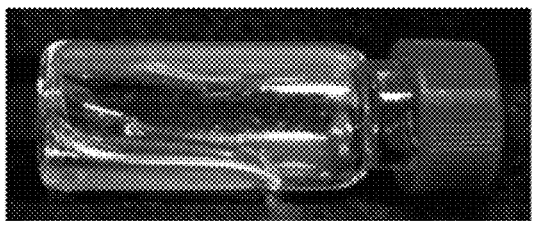
FIGS. 18A-18F were optical images of 1F-FF/PEG300, 1F-FF/PEG600, 1F-FF/PEG1000, 1F-FF/PEG1500, 1F-FF/PEG2000, and 1F-FF/PEG3000 according to some embodiments of the invention during the period of gel-to-sol.
Figure 18B:
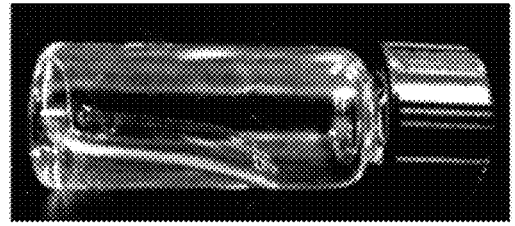
Figure 18C:
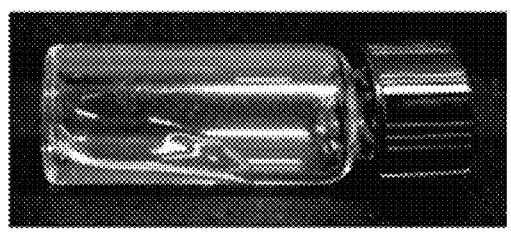
Figure 18D:
Figure 18E:
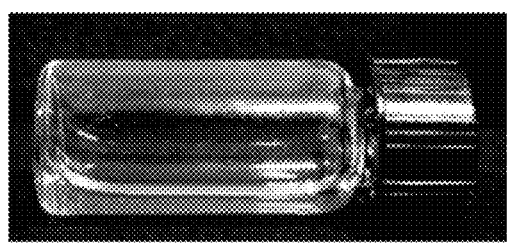
Figure 18F:
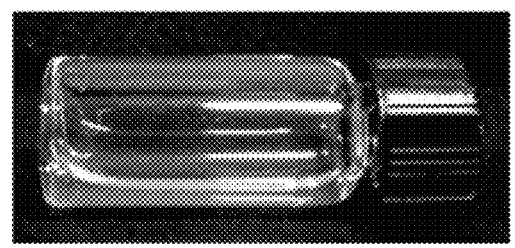

In some embodiments of the invention, accordingly, with the remaining conditions the same, the analysis was further performed by a rheological instrument, and the results thereof were shown in FIGS. 16A-16B and 17A-17B. FIG. 16A was a diagram showing rheological behavior of a hydrogel 0.5 wt % 3F-FF according to some embodiments of the invention, FIG. 16B was a diagram showing rheological behavior of a solution of 0.5 wt %: 4.5 wt % 3F-FF/PEG according to some embodiments of the invention, FIG. 17A was a diagram showing rheological behavior of a hydrogel 0.5 wt % 1F-FF according to some embodiments of the invention, and FIG. 17B was a diagram showing rheological behavior of a solution of 1 wt %: 4 wt % 1F-FF/PEG according to some embodiments of the invention.

Referring to FIGS. 16A-16B and 17A-17B, it showed that no matter at 25° C. or 60° C., the storage modulus (G', $2.23\times10^2$ Pa) of the 0.5 wt % 3F-FF with the pH value of 7 was greater than the loss modulus (G", $2.24\times10^1$ Pa) thereof, which represented that the 0.5 wt % 3F-FF was a stable hydrogel. Meanwhile, both of the G' and the G" of the 4.5 wt % PEG1500 (30 Mm) were very low, which represented that the 4.5 wt % PEG1500 was a viscous liquid that behaved like a solution. Once the 3F-FF and the PEG1500 were mixed at a mixing ratio of 1 wt %:4 wt %, as the temperature rises, the G' and the G" increase sharply, which represented a solid-like behavior with greater elasticity when beyond the critical temperature point. The values of the G' and the G" increased continuously from 30° C. to 50° C. till the final stage of the plateau, which represented the formation of the stable hydrogel with a certain mechanical strength. The result supported the characteristics (G', $1.12\times10^4$ Pa and G", $1.92\times10^3$ Pa) of the thermosensitive supramolecular DN fibers of the 3F-FF/PEG1500 that transformed into the stable hydrogel at 37° C. At 25° C., the G' of the 1F-FF/PEG1500 was $2.56\times10^2$ Pa and the G" the 1F-FF/PEG1500 was $5.07\times10^1$ Pa; at 37° C., the G' of the 1F-FF/PEG1500 was $5.09\times10^3$ Pa and the G" was $2.83\times10^2$ Pa. In addition, at 25° C., the G' of the 1 wt % 0F-FF was $2.56\times10^1$ Pa and the G" of the 1 wt % 0F-FF was $3.07\times10^0$ Pa, and at 25° C., the G' of the 1 wt % 0F-FF was $5.09\times10^2$ Pa and the G" of the 1 wt % 0F-FF was $2.83\times10^1$ Pa.

In some embodiments of the invention, in order to better understand the excellent characteristics of the 1F-FF/PEG, the 1F-FF mixed with the PEG of different molecular weight were further analyzed for a gel-sol behavior, and the results thereof were shown in FIGS. 18A-18F, 19A-19F and Table 6. FIGS. 18A-18F were optical images of 1F-FF/PEG300, 1F-FF/PEG600, 1F-FF/PEG1000, 1F-FF/PEG1500, 1F-FF/PEG2000, and 1F-FF/PEG3000 according to some embodiments of the invention during the period of gel-to-sol, and FIGS. 19A-19F were TEM images of 1F-FF/PEG300, 1F-FF/PEG600, 1F-FF/PEG1000, 1F-FF/PEG1500, 1F-FF/ PEG2000, and 1F-FF/PEG3000 according to some embodiments of the invention, respectively.

TABLE 6

| Samples | pH | State at 37° C. | State at 0° C. (Surrounded by ice cubes) | Detailed description of the sample |
| --- | --- | --- | --- | --- |
| 1F-FF | 7.0 | Gel | Gel | Still hydrosol |
| 1F-FF/PEG300 | 7.0 | Gel | Solution after 15 minutes | Small pieces of hydrogel were present in the viscous solution |
| 1F-FF/PEG600 | 7.0 | Gel | Solution after 15 minutes | Small pieces of hydrogel were present in the viscous solution |
| 1F-FF/PEG1000 | 7.0 | Gel | Solution after 15 minutes | Small pieces of hydrogel were present in the viscous solution |
| 1F-FF/PEG1500 | 7.0 | Gel | Solution after 15 minutes | Clear solution |
| 1F-FF/PEG2000 | 7.0 | Gel | Solution after 15 minutes | Clear solution |
| 1F-FF/PEG3000 | 7.0 | Gel | Solution after 15 minutes | Clear solution |

Referring to FIGS. 18A-18F, 19A-19F, and Table 6, it showed that in a mixture of the 1F-FF and the PEG with different molecular weights, the PEG1500, the PEG2000, and the PEG3000 had the similar gel-sol time, that is, 15 minutes. Assuming the application in the cell culture, the cells might need to be released from the matrix. The cells encapsulated in the DNH fibers could be released by disrupting the fiber network of the hydrogel. To confirm the above assumption, the TEM image of the 1F-FF was analyzed after the gel was converted into a transparent solution under a cooler environment, such as 0° C. It showed that no self-assembled fibers of the 1F-FF could be observed, and no co-fibers of the PEG could be seen. Therefore, it could be used to support and explain the phenomenon that the fibers were destroyed after the gel was converted into a transparent solution. In addition, the gel-sol behavior was monitored by changing the rheological temperature from high to low (60-0° C.). The results thereof show that the gel-sol transition decreased sharply when the temperature was lower than 20° C. In the range of high temperature, the G' and the G" were both very high, and the G" was much greater than the G' when in range of high temperature, which represented that the behavior of the hydrogel. As the temperature decreased to the transition point, both the G' and the G" decreased sharply to a cross point where the G' started to be less than the G", which represented that a transparent liquid that behaved like a solution. As the temperature further decreased, the G' continued to be decreased and less than the G", which represented that the energy was not sufficient to be stored, so it became apparently a solution.

In other embodiments of the invention, a testing for the hydrogel property was performed on the peptide 5F-FFRGD of the Embodiment 5, and the results thereof were shown in Table 7

TABLE 7

| Samples | 5F-FFRGD/ PEG1500 mg/mg | *wt % | Total volume (mL) | pH | 25° C. | 37° C. | min** |
|---|---|---|---|---|---|---|---|
| 1 | 2:0 | 0.5 | 0.4 | 7.0 | Sol | Sol | 10 |
| 2 | 2:2 | 1 | 0.4 | 7.0 | Sol | Gel | 10 |
| 3 | 2:6 | 2 | 0.4 | 7.0 | Sol | Gel | 10 |
| 4 | 2:10 | 3 | 0.4 | 7.0 | Sol | Gel | 10 |
| 5 | 2:14 | 4 | 0.4 | 7.0 | Sol | Gel | 10 |
| 6 | 2:18 | 5 | 0.4 | 7.0 | Sol | Gel | 10 |

*Concentration of GHAVD
**Time required for the gel-sol transition

Figure 20:
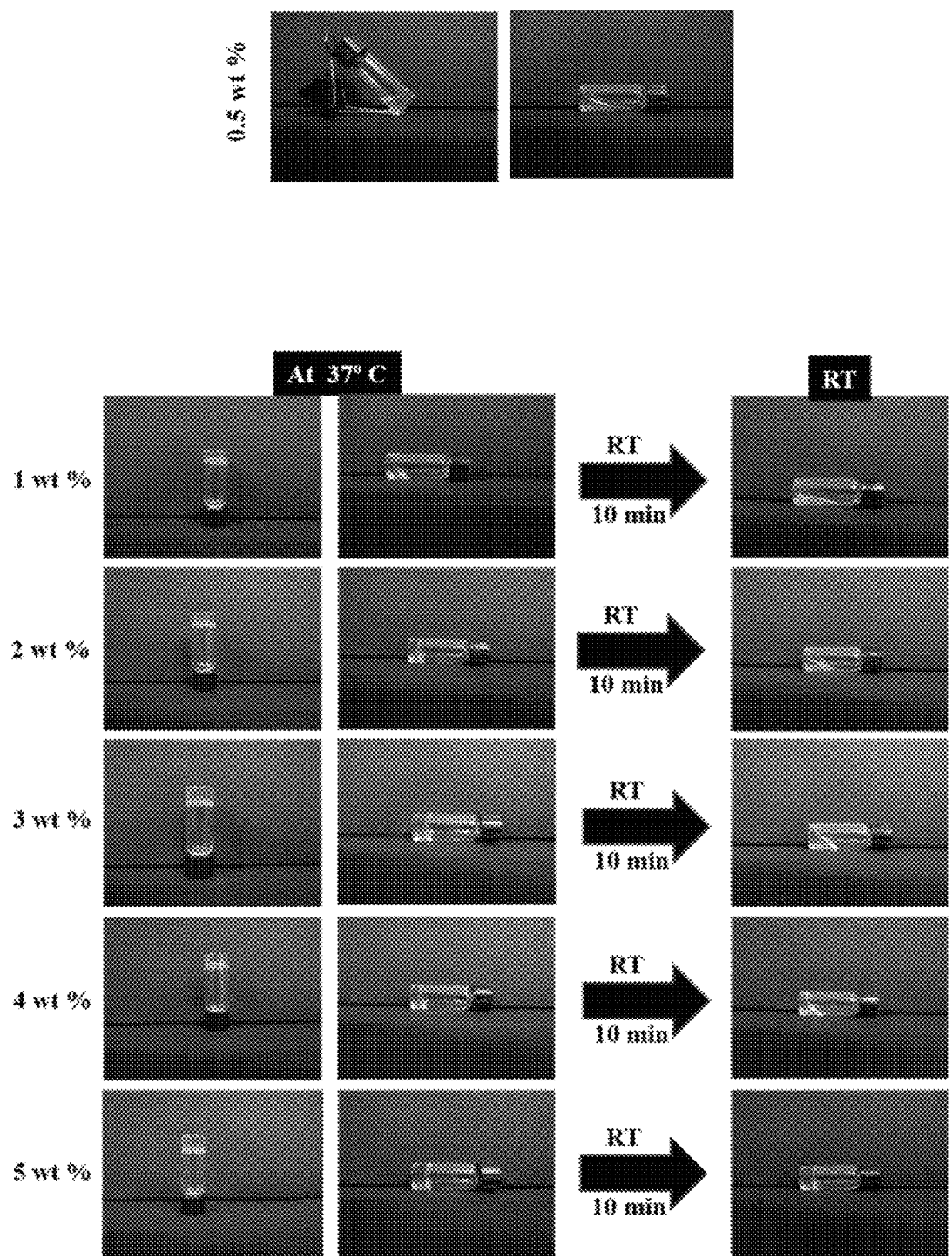
FIG. 20 showed optical images indicating thermal sensitivities of a peptide 5F-FF RGD according to some embodiments of the invention.

FIG. 20 showed optical images indicating thermal sensitivities of a peptide 5F-FF RGD according to some embodiments of the invention. In FIG. 20, it showed that regardless of the concentration of the peptide 5F-FFRGD, it could be converted again into a sol state after being already converted into a gel at 37° C. and left at room temperature for 20 minutes.

In other embodiments of the invention, a testing for the hydrogel property was performed on the peptide 5F-FFGHAVD of the Embodiment 7, and the results thereof were shown in Table 8.

TABLE 8

| Samples | 5F-FFGHAVD/ PEG1500 mg/mg | *wt % | Total volume (mL) | pH | 25° C. | 37° C. | min** |
|---|---|---|---|---|---|---|---|
| 1 | 2:0 | 0.5 | 0.4 | 7.0 | Sol | Sol | 20 |
| 2 | 2:2 | 1 | 0.4 | 7.0 | Sol | Gel | 20 |
| 3 | 2:6 | 2 | 0.4 | 7.0 | Sol | Gel | 20 |
| 4 | 2:10 | 3 | 0.4 | 7.0 | Sol | Gel | 20 |
| 5 | 2:14 | 4 | 0.4 | 7.0 | Sol | Gel | 20 |
| 6 | 2:18 | 5 | 0.4 | 7.0 | Sol | Gel | 20 |

*Concentration of PFB-FFGHAVD
**Time required for the gel-sol transition

Figure 21:
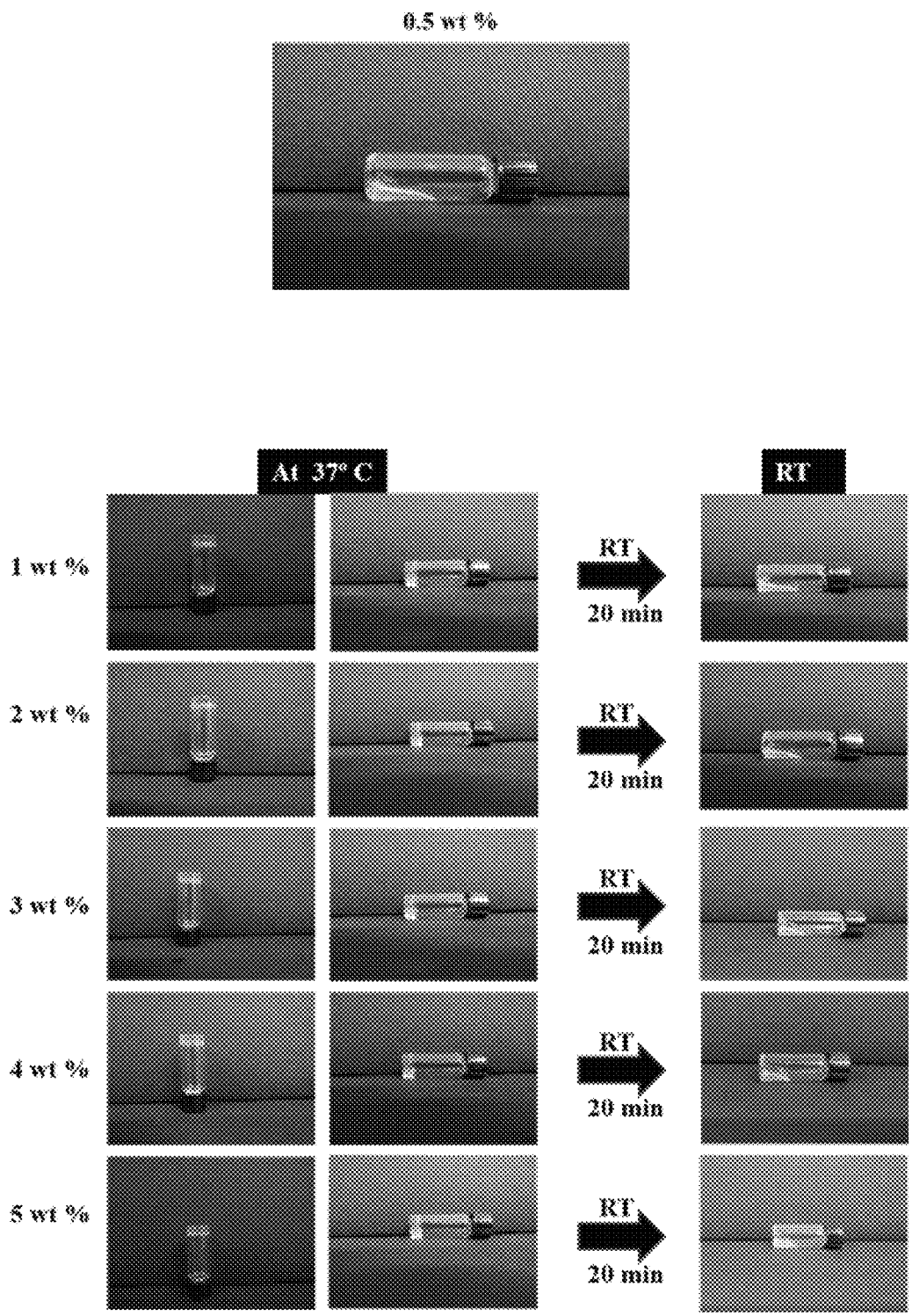
FIG. 21 showed optical images indicating thermal sensitivities of a peptide 5F-FF GHAVD according to some embodiments of the invention.

FIG. 21 showed optical images indicating thermal sensitivities of a peptide 5F-FF GHAVD according to some embodiments of the invention. In FIG. 21, it showed that regardless of the concentration of the peptide 5F-FFGHAVD, it could be converted again into a sol state after being already converted into a gel at 37° C. and left at room temperature for 20 minutes.

In summary, the thermosensitive peptide hydrogel according to some embodiments of the invention could match the rigidity of the tissue to be simulated by adjusting the mixing ratio of the compounds, and might have the characteristics of a nanofiber structure, thermal sensitivity, and thermal reversibility at the same time. The above description is exemplary only, and not restrictive. Any equivalent modification or change made without departing from the spirit and scope of the invention shall be included in the scope of the claims.

What is claimed is:

1. A thermosensitive peptide hydrogel, comprising:
   water;
   at least a polymer of a polyether or a polyol; and
   a peptide molecule having a chemical structure as shown in chemical formula (1) below:

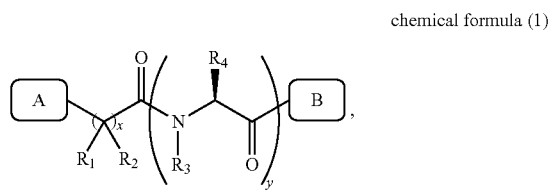

chemical formula (1)

wherein A is a molecular moiety with at least one aromatic group substituted with 0-5 identical or different halogen atoms, and the halogen atoms are independently fluorine, chlorine, bromine, or iodine atoms;
$R_1$ and $R_2$ are each independently hydrogen, a substituted or unsubstituted $C_1$-$C_{16}$ alkyl group;
$R_3$ and $R_4$ are each independently hydrogen, $C_1$-$C_{10}$ alkyl, $C_7$-$C_{10}$ aralkyl, $C_2$-$C_{10}$ alkylthioalkyl, $C_7$-$C_{10}$ hydroxyaralkyl, $C_6$-$C_{10}$ heteroaralkyl, $C_2$-$C_{10}$ carboxyalkane, $C_2$-$C_{10}$ guanidylalkyl or $C_1$-$C_{10}$ aminoalkyl;
B is —OH, —OR$_5$, wherein R$_5$ is hydrogen, alkyl, aralkyl, alkylthioalkyl, hydroxyaralkyl, heteroaralkyl, carboxyalkyl, guanidylalkyl, glycosyl, or oligonucleic acid groups;
x is an integer from 0-10, and each $R_1$ or $R_2$ is identical or different; and
y is an integer from 1-20, and each $R_3$ or $R_4$ is identical or different.

2. The thermosensitive peptide hydrogel of claim 1, wherein a concentration of the peptide molecules in the thermosensitive peptide hydrogel is at least 100 nM and not more than 30 wt %.

3. The thermosensitive peptide hydrogel of claim 1, wherein the halogen atoms are fluorine atom.

4. The thermosensitive peptide hydrogel as in claim 1, wherein the polymer of the polyether or polyol comprises poly[ethylene glycol], polyalkylene glycol, polyvinyl alcohol (PVA), poly[propylene glycol], polyester polyol, polyphenylene oxide, poly[ethylene vinyl-co-alcohol], EVOH), polysaccharide, or any combinations thereof.

5. The thermosensitive peptide hydrogel as in claim 1, wherein the thermosensitive peptide hydrogel is a liquid at 2-30° C., and a hydrogel when above 30° C.

6. The thermosensitive peptide hydrogel as in claim 1, wherein the thermosensitive peptide hydrogel has a storage modulus of 0.1-$10^7$ Pa at 37° C.

7. The thermosensitive peptide hydrogel as in claim 1, wherein the thermosensitive peptide hydrogel is thermally reversible.

8. The thermosensitive peptide hydrogel as in claim 1, wherein the glycosyl group contained in the peptide molecule is mannosyl, oligosaccharide, fructosyl, galactosyl, or any combinations thereof.

* * * * *